United States Patent
Nakayama et al.

(10) Patent No.: US 8,314,258 B2
(45) Date of Patent: Nov. 20, 2012

(54) METHOD FOR PRODUCING ACRYLATE DERIVATIVE, ACRYLATE DERIVATIVE, AND INTERMEDIATE THEREOF

(75) Inventors: Osamu Nakayama, Niigata (JP); Takashi Fukumoto, Niigata (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 233 days.

(21) Appl. No.: 12/918,527

(22) PCT Filed: Feb. 20, 2009

(86) PCT No.: PCT/JP2009/052998
§ 371 (c)(1),
(2), (4) Date: Aug. 23, 2010

(87) PCT Pub. No.: WO2009/104727
PCT Pub. Date: Aug. 27, 2009

(65) Prior Publication Data
US 2011/0009643 A1  Jan. 13, 2011

(30) Foreign Application Priority Data
Feb. 22, 2008  (JP) ................................ 2008-041010

(51) Int. Cl.
*C07D 339/00* (2006.01)
(52) U.S. Cl. ........................................................ 549/11
(58) Field of Classification Search ............... 549/11
See application file for complete search history.

(56) References Cited

FOREIGN PATENT DOCUMENTS

| | | |
|---|---|---|
| JP | 2 59570 | 2/1990 |
| JP | 5 88367 | 4/1993 |
| JP | 7 295221 | 11/1995 |
| JP | 9 73173 | 3/1997 |
| JP | 2003 246825 | 9/2003 |
| JP | 2008 138073 | 6/2008 |
| WO | 2007 094474 | 8/2007 |

OTHER PUBLICATIONS

Satoshi Takechi, et al., "Impact of 2-Methyl-2-Adamantyl Group Used for 193-nm Single-Layer Resist", Journal of Photopolymer Science and Technology, vol. 9, No. 3, 1996, pp. 475-487.
International Technology Roadmap for Semiconductors 2006 Update Lithography, 2 front pages, pp. 1-18.
Idriss Blakey, et al., "Synthesis of High Refractive Index Sulfur Containing Polymers for 193nm Immersion Lithography; A Progress Report", Proc. of SPIE, vol. 6153, 2006, pp. 61530H-1 to 61530H-10.
Will Conley, "Everything You Ever Wanted to Know About Why the Semiconductor Industry Needs a High Refractive Index Photoresist . . . But Were Afraid to Ask, Part 1" Proc. of SPIE, vol. 6153, 2006, pp. 61531L-1 to 61531L-9.
Antolini, L., et al., "The Reaction of the Acetates of α-Chloro Methyl Hemiacetals with Nucleophiles. Synthesis of 2-Hydroxy-1, 4-Dithianes," Gazzetta Chimica Italiana, vol. 127, pp. 11-17, (1997).
Fujihara, H., et al., "Mechanistic Investigation on the Remote Pummerer Reaction of 1,5-Dithiacyclooctane 1-Oxide with Acetic Anhydride via Intermediate Formation of Disulphide Dication," Gazzetta Chimica Italiana, vol. 119, pp. 617-620, (1989).
International Search Report issued May 26, 2009 in PCT/JP09/052998 filed Feb. 20, 2009.
U.S. Appl. No. 12/918,689, filed Aug. 20, 2010, Nakayama, et al.
U.S. Appl. No. 12/918,675, filed Aug. 23, 2010, Sato, et al.

*Primary Examiner* — Taofiq A Solola
(74) *Attorney, Agent, or Firm* — Oblon, Spivak, McClelland, Maier & Neustadt, L.L.P.

(57) ABSTRACT

Provided are 1) a production process for an acrylic ester derivative capable of being a raw material of a polymer for obtaining a photoresist composition capable of forming a photoresist film which is excellent in a reactivity to acid and a heat stability and is less swollen in developing and which has a refractive index of preferably 1.72 or more in 193 nm and can be patterned, 2) an acrylic ester derivative obtained by the above production process and 3) alcohol and ester which are synthetic intermediates for the above acrylic ester derivative.

4 Claims, 1 Drawing Sheet

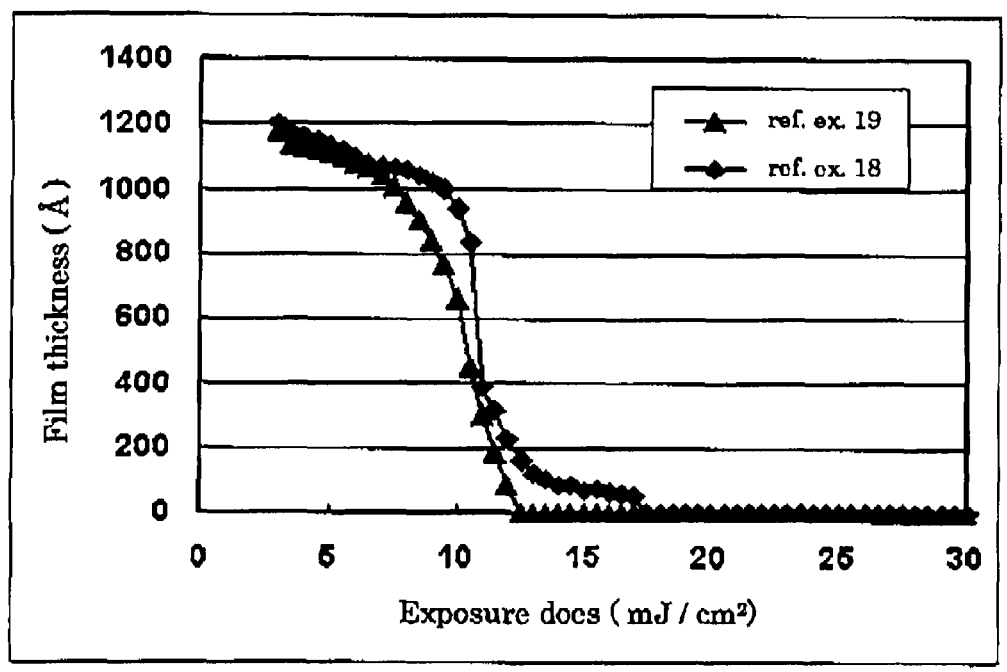

METHOD FOR PRODUCING ACRYLATE DERIVATIVE, ACRYLATE DERIVATIVE, AND INTERMEDIATE THEREOF

TECHNICAL FIELD

The present invention relates to a production process for acrylic ester derivatives, acrylic ester derivatives and intermediates thereof. The acrylic ester derivatives obtained in the present invention are useful as raw materials for polymers obtained, for example, by polymerizing the above acrylic ester derivative as one of raw materials and photoresist compositions obtained by using the above acrylic ester derivative as a component. Further, Alcohols and esters obtained in the present invention are useful as intermediates for the above acrylic ester derivatives.

BACKGROUND ART

In recent years, electronic devices are highly required to be increased in integration in the electronic device production field represented by integrated circuit device production, and this allows a photolithographic technique for forming fine patterns to be required. Accordingly, photoresist compositions corresponding to photolithography using as exposure light, radial rays having a wavelength of 200 nm or less such as an ArF excimer laser (wavelength: 193 nm), an $F_2$ excimer laser (wavelength: 157 nm) and the like are actively developed, and proposed are a large number of chemically amplified photoresist compositions comprising polymer having an acid-dissociable functional group and compounds (herein referred to as "a photoacid generator") generating acid by irradiation (herein referred to as "exposure") of a radial ray. The above polymer having an acid-dissociable functional group comprises a basic structure in which a part of an alkali-readily soluble site of an alkali-soluble polymer is protected by a suitable acid-dissociable functional group, and selection of the above acid-dissociable functional group is very important in terms of controlling the performances of the photoresist composition.

Known as the existing acid-dissociable functional group are 1) groups having an adamantane structure (refer to a patent document 1 and a non-patent document 1) and 2) groups comprising a tetrahydropyranyl group (refer to a patent document 2). The acid-dissociable functional group is required to allow a high reactivity to acids to be consistent with a stability in which it is not decomposed at a baking step and requested to have a heat stability of 130° C. or higher (refer to a non-patent document 3). The tetrahydropyranyl group in 2) has the advantage that it has a high reactivity in terms of an acid dissociation, but it is lacking in a heat stability and is not satisfactory in a fundamental performance of the resist.

One of large problems of lithographic techniques in recent years includes line width variation of formed patterns which is called a line width roughness (herein referred to as "LWR"), and an allowable value thereof is required to be less than 8% of a line width (refer to a non-patent document 3). It is necessary for improving LWR to inhibit patterns—from being deformed by swelling, that is, to allow a polymer which is a photoresist composition component to be less liable to be swollen.

A polymer into which 1) the group having an adamantane structure is introduced as the acid-dissociable functional group has a high reactivity to acids and a heat stability. However, the above polymer has a high hydrophobicity and is not satisfactory in an affinity with a developer to allow parts which are not dissolved in developing to remain in an exposed area, and it brings about swelling to result in causing a problem of increasing LWR. Accordingly, polymers for a photoresist composition which are less liable to be swollen are still anxious to be developed, and the existing situation is that compounds having an acid-dissociable functional group for achieving the above matter are strongly anxious to be developed.

Further, finer resist patterns (for example, fine resist patterns having a line width of about 90 nm) shall be required to be formed in the future. In order to achieve formation of resist patterns having a finer line width than 90 nm, it is considered to shift a wavelength of a light source in an exposure equipment to a shorter region and increase a numerical aperture (NA) of a lens. However, a new expensive exposure equipment is required for shifting a wavelength of a light source to a shorter region. Further, in an increase in a numerical aperture of a lens, a resolution and a depth of focus in a relation of trade-off, and therefore the problem that the depth of focus is reduced even if the resolution is elevated is involved therein.

In recent years, a method called a liquid immersion lithography is reported as a lithographic technique which makes it possible to solve the above problem. This method is a method in which purified water or a liquid refractive medium (immersion liquid) such as a fluorinated inert liquid having a prescribed thickness is allowed to be present at least on a photoresist film between a lens and a photoresist film on a substrate in exposure. In the above method, even if a light source having the same exposing wavelength is used, a higher resolving property is achieved (provided with a high resolution) as well as having no change in a depth of focus as is the case with an instance in which a light source having a shorter wavelength is used and an instance in which a high NA lens is used by substituting an space of exposure optical path which has so far been an inert gas such as air and nitrogen with a liquid having a larger refractive index (n), for example, purified water and the like. Use of the above liquid immersion lithography makes it possible to achieve formation of a resist pattern which is formed at a lower cost and is excellent in a higher resolving property and which is excellent as well in a depth of focus by using a lens mounted in an existing equipment, and therefore it attracts attentions very much.

On the other hand, if a refractive index of a liquid refractive index medium (immersion liquid) is higher than a refractive index of, for example, a photoresist film in a liquid immersion lithographic process, light is less liable to be incident from an immersion liquid into the photoresist film according to a Snell's law. Accordingly, the fundamental performances such as the sensitivity and the like are likely to be deteriorated. Further, if an immersion liquid has a high refractive index, a difference in a refractive index between the immersion liquid and the photoresist film is increased, and light is reflected wholly on an interface between the immersion liquid and the photoresist film. Accordingly, since light is not incident completely into the photoresist film, the sufficiently high sensitivity is not obtained, and it is anticipated that a throughput in a resist process is notably reduced.

Then, it is proposed that particularly when an immersion liquid (immersion liquid having a high refractive index) having a refractive index of 1.70 or more in a wavelength of 193 nm is used, a photoresist film having a higher refractive index than that of the above immersion liquid is used (refer to non-patent documents 4 and 5).

Patent document 1: Japanese Patent Application Laid-Open No. 73173/1997

Patent document 2: Japanese Patent Application Laid-Open No. 88367/1993

Non-patent document 1: Journal of Photopolymer Science and Technology, Vol. 9, No. 3, p. 475 to 487 (1996)

Non-patent document 2: ITRS 2006, UP DATE version, part of lithography, p. 8

Non-patent document 3: ITRS 2006, UP DATE version, part of lithography, p. 7

Non-patent document 4: SPIE 2006 61530H

Non-patent document 5: SPIE 2006 61531L

DISCLOSURE OF THE INVENTION

Problems to be Solved by the Invention

The photoresist films formed by the materials (photoresist compositions) described in the non-patent documents 4 and 5 have a high refractive index in a wavelength of 193 nm, but they can not form resist patterns and are not provided with performances of a photoresist film. Accordingly, photoresist compositions which can form a photoresist film having a high refractive index (for example, a refractive index of 1.72 or more) in a wavelength of 193 nm and which provide a photoresist film capable of being patterned are anxious to be developed.

In order to solve the problems described above, the present invention has been made by paying attentions on an acid-dissociable functional group of a compound having an acid-dissociable functional group and intensely investigating it. The object of the present invention is to provide 1) a production process for an acrylic ester derivative capable of being a raw material of a polymer for obtaining a photoresist composition capable of forming a photoresist film which is excellent in a reactivity to acid and a heat stability and is less swollen in developing and which has a refractive index of preferably 1.72 or more in 193 nm and can be patterned, 2) an acrylic ester derivative obtained by the above production process and 3) alcohol and ester which are synthetic intermediates for the above acrylic ester derivative.

Means for Solving the Problems

That is, the present invention is achieved by providing:

1. a production process for an acrylic ester derivative (hereinafter referred to as an acrylic ester derivative (1)) represented by Formula (1) shown below:

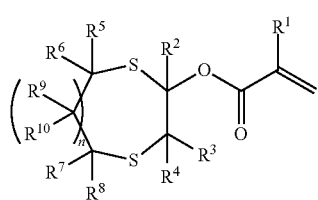

(1)

(wherein n, $R^1$, $R^2$, $R^3$, $R^4$, $R^5$, $R^6$, $R^7$, $R^8$, $R^9$ and $R^{10}$ are the same as defined below), comprising the steps of: reacting dithiol (hereinafter referred to as dithiol (2)) represented by Formula (2) shown below with a base:

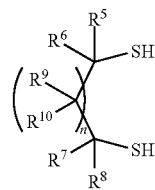

(2)

wherein in n, $R^5$, $R^6$, $R^7$, $R^8$, $R^9$ and $R^{10}$, 1) when n is 0, $R^5$ and $R^8$ each represent independently a hydrogen atom, a linear alkyl group having 1 to 6 carbon atoms, a branched alkyl group having 3 to 6 carbon atoms or a cyclic alkyl group having 3 to 6 carbon atoms; $R^6$ and $R^7$ each represent independently a hydrogen atom, a linear alkyl group having 1 to 6 carbon atoms, a branched alkyl group having 3 to 6 carbon atoms or a cyclic alkyl group having 3 to 6 carbon atoms or $R^6$ and $R^7$ are combined to represent an alkylene group having 3 to 6 carbon atoms; or 2) when n is 1 or 2, $R^5$, $R^6$, $R^7$, $R^8$, $R^9$ and $R^{10}$ each represent independently a hydrogen atom, a linear alkyl group having 1 to 6 carbon atoms, a branched alkyl group having 3 to 6 carbon atoms or a cyclic alkyl group having 3 to 6 carbon atoms); then reacting the reaction product with halide (hereinafter referred to as halide (4)) represented by Formula (4) shown below:

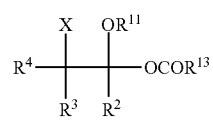

(4)

(wherein combination of $R^2$, $R^3$ and $R^4$ is any of:

1) $R^2$, $R^3$ and $R^4$ each represent independently a hydrogen atom, a linear alkyl group having 1 to 6 carbon atoms, a branched alkyl group having 3 to 6 carbon atoms or a cyclic alkyl group having 3 to 6 carbon atoms;

2) $R^2$ and $R^3$ are combined to represent an alkylene group having 3 to 6 carbon atoms, and $R^4$ represents a hydrogen atom, a linear alkyl group having 1 to 6 carbon atoms, a branched alkyl group having 3 to 6 carbon atoms or a cyclic alkyl group having 3 to 6 carbon atoms; or 3) $R^2$ represents a hydrogen atom, a linear alkyl group having 1 to 6 carbon atoms, a branched alkyl group having 3 to 6 carbon atoms or a cyclic alkyl group having 3 to 6 carbon atoms, and $R^3$ and $R^4$ are combined to represent an alkylene group having 3 to 6 carbon atoms;

$R^{11}$ represents a linear alkyl group having 1 to 3 carbon atoms or a branched alkyl group having 3 to 6 carbon atoms; X represents a chlorine atom, a bromine atom or an iodine atom; and $R^{13}$ represents a linear alkyl group having 1 to 6 carbon atoms, a branched alkyl group having 3 to 6 carbon atoms or a cyclic alkyl group having 3 to 6 carbon atoms) to obtain eater (hereinafter referred to as eater (6)) represented by Formula (6) shown below with a base:

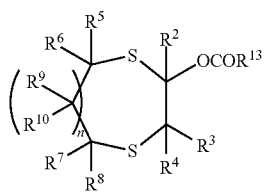

(6)

(wherein n, $R^2$, $R^3$, $R^4$, $R^5$, $R^6$, $R^7$, $R^8$, $R^9$, $R^{10}$ and $R^{13}$ are the same as defined above);
hydrolyzing the above eater (6) to obtain alcohol (hereinafter referred to as alcohol (5)) represented by Formula (5) shown below:

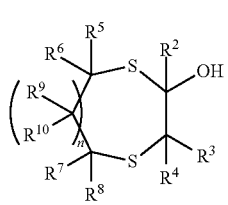

(5)

(wherein n, $R^2$, $R^3$, $R^4$, $R^5$, $R^6$, $R^7$, $R^8$, $R^9$ and $R^{10}$ are the same as defined above); and
then reacting the above alcohol with a polymerizable group-introducing agent represented by a formula $CH_2=CR^1COX^1$ (wherein $R^1$ is a hydrogen atom, methyl or trifluoromethyl, and $X^1$ represents a chlorine atom, a bromine atom or an iodine atom), a formula $(CH_2=CR^1CO)_2O$ (wherein $R^1$ is the same as described above), a formula $CH_2=CR^1COOC(=O)R^{14}$ (wherein $R^1$ is the same as described above, and $R^{14}$ represents t-butyl or 2,4,6-trichlorophenyl) or a formula $CH_2=CR^1COOSO_2R^{15}$ (wherein $R^1$ is the same as described above, and $R^{16}$ represents methyl or p-tolyl) in the presence of a basic substance,
2. the production process for an acrylic ester derivative (1) according to the above item 1, wherein the base reacted with the ditiol is sodium hydride,
3. a production process for an acrylic ester derivative (1), comprising the steps of:
reacting the dithiol (2) with a base;
then reacting the reaction product with the halide (4) to obtain the alcohol (5); and then
reacting the above alcohol (5) with a polymerizable group-introducing agent represented by a formula $CH_2=CR^1COX^1$ (wherein $R^1$ is the same as described above), a formula $(CH_2=CR^1CO)_2O$ (wherein $R^1$ is the same as described above), a formula $CH_2=CR^1COOC(=O)R^{14}$ (wherein $R^1$ and $R^{14}$ are the same as described above) or a formula $CH_2=CR^1COOSO_2R^{15}$ (wherein $R^1$ and $R^{15}$ are the same as described above) in the presence of a basic substance,
4. the production process for an acrylic ester derivative (1) according to the above item 3, wherein the base reacted with the ditiol is sodium hydride,
5. an acrylic ester derivative (1),
6. an alcohol (5),
7. an ester (6),
8. the acrylic ester derivative (1) according to the above item 5, wherein n is 0 or 1, and $R^3$ is a hydrogen atom,
9. the acrylic ester derivative (1) according to the above item 5, wherein n is 0 or 1, and $R^2$, $R^3$, $R^4$, $R^5$, $R^6$, $R^7$, $R^8$, $R^9$ and $R^{10}$ are a hydrogen atom or methyl,
10. the alcohol (5) according to the above item 6, wherein n is 0 or 1,
11. the alcohol (5) according to the above item 6, wherein n is 0 or 1, and $R^2$, $R^3$, $R^4$, $R^5$, $R^6$, $R^7$, $R^8$, $R^9$ and $R^{10}$ are a hydrogen atom or methyl,
12. the ester (6) according to the above item 7, wherein n is 0 or 1 and
13. the ester (6) according to the above item 7, wherein n is 0 or 1, and $R^2$, $R^3$, $R^4$, $R^5$, $R^6$, $R^7$, $R^8$, $R^9$ and $R^{10}$ are a hydrogen atom or methyl.

Effect of the Invention

According to the present invention, capable of being provided are 1) a production process for an acrylic ester derivative capable of being a raw material of a polymer for obtaining a photoresist composition capable of forming a photoresist film which is excellent in a reactivity to acid and a heat stability and is less swollen in developing and which has a refractive index of preferably 1.72 or more in 193 nm and can be patterned, 2) an acrylic ester derivative obtained by the above production process and 3) alcohol and ester which are synthetic intermediates for the above acrylic ester derivative.

BRIEF EXPLANATION OF THE DRAWINGS

FIG. 1 is a drawing showing a correlation of an exposure dose of light radiated on photoresist films formed by photoresist compositions (b) and (d) obtained in Reference Examples 2 and 3 with the film thicknesses of the above photoresist films (refer to Reference Examples 18 and 19).

BEST MODE FOR CARRYING OUT THE INVENTION

Acrylic Ester Derivative (1):
$R^1$ in the acrylic ester derivative (1) represents a hydrogen atom, methyl or trifluoromethyl. $R^1$ is preferably a hydrogen atom or methyl, more preferably methyl.
Combination of $R^2$, $R^3$ and $R^4$ in the acrylic ester derivative (1) is any of 1), 2) and 3) shown below:
1) $R^2$, $R^3$ and $R^4$ each represent independently a hydrogen atom, a linear alkyl group having 1 to 6 carbon atoms, a branched alkyl group having 3 to 6 carbon atoms or a cyclic alkyl group having 3 to 6 carbon atoms;
2) $R^2$ and $R^3$ are combined to represent an alkylene group having 3 to 6 carbon atoms, and $R^4$ represents a hydrogen atom, a linear alkyl group having 1 to 6 carbon atoms, a branched alkyl group having 3 to 6 carbon atoms or a cyclic alkyl group having 3 to 6 carbon atoms; and
3) $R^2$ represents a hydrogen atom, a linear alkyl group having 1 to 6 carbon atoms, a branched alkyl group having 3 to 6 carbon atoms or a cyclic alkyl group having 3 to 6 carbon atoms, and $R^3$ and $R^4$ are combined to represent an alkylene group having 3 to 6 carbon atoms.

The above linear alkyl groups having 1 to 6 carbon atoms include, for example, methyl, ethyl, n-propyl, n-butyl, n-pentyl, n-hexyl and the like in all cases. The above branched alkyl groups having 3 to 6 carbon atoms include, for example, isopropyl, isobutyl, sec-butyl and the like in all cases. The above cyclic alkyl groups having 3 to 6 carbon atoms include, for example, cyclopropyl, cyclobutyl, cyclopentyl, cyclohexyl and the like in all cases.
The alkylene group having 3 to 6 carbon atoms in a case where $R^2$ and $R^3$ are combined includes, for example, propane-1,3-diyl, butane-1,4-diyl, pentane-1,5-diyl, hexane-1,6-diyl and the like. Among them, butane-1,4-diyl is preferred.

The alkylene group having 3 to 6 carbon atoms in a case where $R^3$ and $R^4$ are combined includes, for example, propane-1,3-diyl, butane-1,4-diyl, pentane-1,5-diyl, hexane-1,6-diyl and the like.

The combination of $R^2$, $R^3$ and $R^4$ is preferably 1) described above, and $R^2$, $R^3$ and $R^4$ each are more preferably a hydrogen atom or methyl, and $R^3$ is particularly preferably a hydrogen atom. All of them are further preferably a hydrogen atom.

In the acrylic ester derivative (1), n, $R^5$, $R^6$, $R^7$, $R^8$, $R^9$ and $R^{10}$ are any of 1) and 2) shown below.

1) When n is 0, $R^5$ and $R^8$ each represent independently a hydrogen atom, a linear alkyl group having 1 to 6 carbon atoms, a branched alkyl group having 3 to 6 carbon atoms or a cyclic alkyl group having 3 to 6 carbon atoms; $R^6$ and $R^7$ each represent independently a hydrogen atom, a linear alkyl group having 1 to 6 carbon atoms, a branched alkyl group having 3 to 6 carbon atoms or a cyclic alkyl group having 3 to 6 carbon atoms or $R^6$ and $R^7$ are combined to represent an alkylene group having 3 to 6 carbon atoms.

2) When n is 1 or 2, $R^5$, $R^6$, $R^7$, $R^8$, $R^9$ and $R^{10}$ each represent independently a hydrogen atom, a linear alkyl group having 1 to 6 carbon atoms, a branched alkyl group having 3 to 6 carbon atoms or a cyclic alkyl group having 3 to 6 carbon atoms.

The above linear alkyl groups having 1 to 6 carbon atoms include, for example, methyl, ethyl, n-propyl, n-butyl, n-pentyl, n-hexyl and the like in all cases. The above branched alkyl groups having 3 to 6 carbon atoms include, for example, isopropyl, isobutyl, sec-butyl and the like in all cases. The above cyclic alkyl groups having 3 to 6 carbon atoms include, for example, cyclopropyl, cyclobutyl, cyclopentyl, cyclohexyl and the like in all cases.

The alkylene group having 3 to 6 carbon atoms in a case where $R^6$ and $R^7$ are combined includes, for example, propane-1,3-diyl, butane-1,4-diyl, pentane-1,5-diyl, hexane-1,6-diyl and the like. Among them, butane-1,4-diyl is preferred.

The term n is preferably 0 or 1, more preferably 0.

When n is 0, $R^5$, $R^6$, $R^7$ and $R^0$ each are preferably a hydrogen atom or methyl. More preferably, all of $R^5$, $R^6$, $R^7$ and $R^8$ are a hydrogen atom, or both of $R^5$ and $R^8$ are methyl, and both of $R^6$ and $R^7$ are a hydrogen atom.

When n is 1, $R^5$, $R^6$, $R^7$, $R^8$, $R^9$ and $R^{10}$ each are preferably a hydrogen atom or methyl, and all of $R^5$, $R^6$, $R^7$, $R^8$, $R^9$ and $R^{10}$ are more preferably a hydrogen atom.

The specific examples of the acrylic ester derivative (1) include, for example, compounds represented by Formulas (1-a) to (1-x) (wherein n is the same as defined above, and p represents 1 or 2), but it shall not be restricted to them.

(1-a)

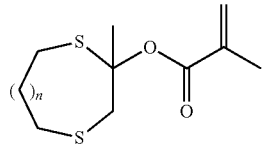

(1-b)

(1-c)

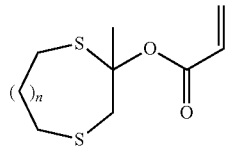

(1-d)

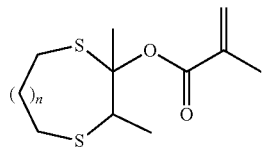

(1-e)

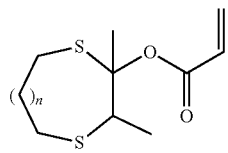

(1-f)

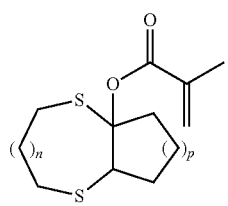

(1-g)

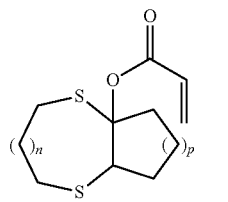

(1-h)

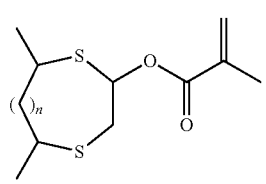

(1-i)

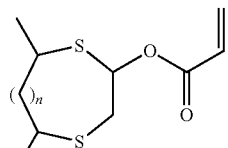

(1-j)

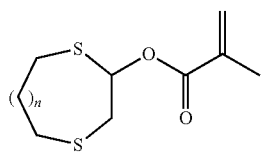

(1-k)

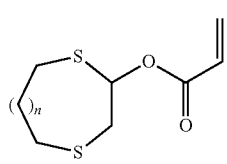

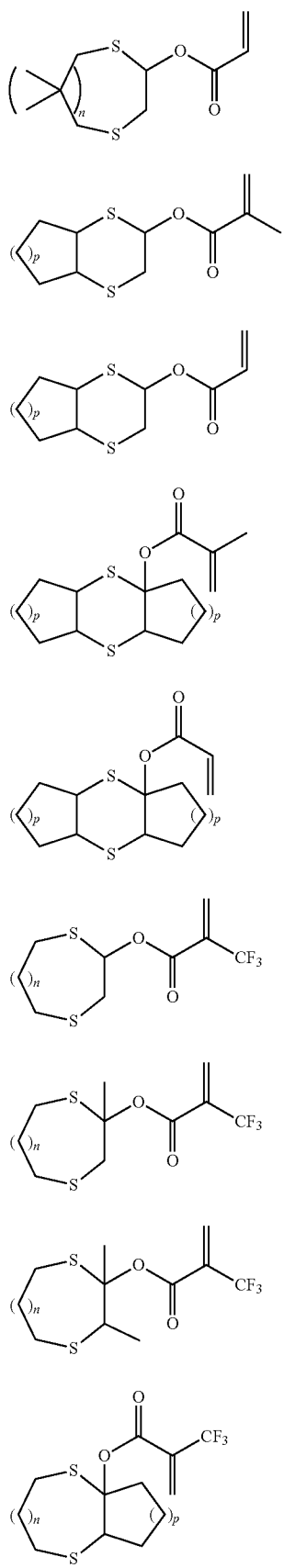
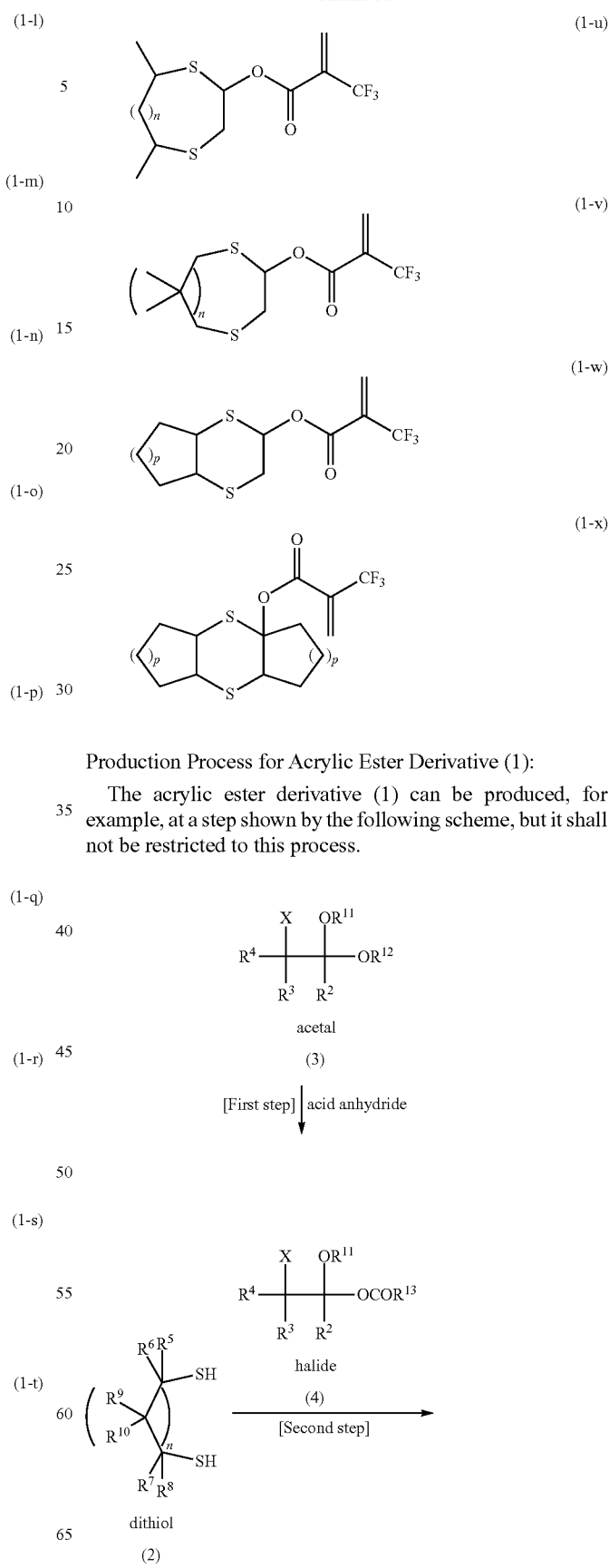
Production Process for Acrylic Ester Derivative (1):
The acrylic ester derivative (1) can be produced, for example, at a step shown by the following scheme, but it shall not be restricted to this process.

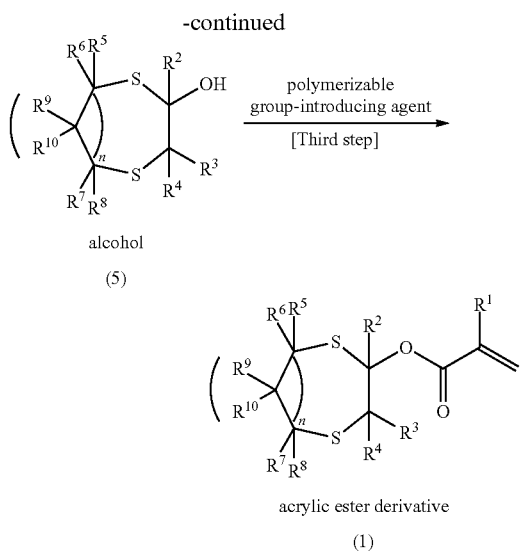

alcohol (5)

acrylic ester derivative (1)

In the scheme described above, n, $R^1$, $R^2$, $R^3$, $R^4$, $R^5$, $R^6$, $R^7$, $R^8$, $R^9$ and $R^{10}$ are the same as defined above. $R^{11}$, $R^{12}$ and $R^{13}$ each represent independently a linear alkyl group having 1 to 3 carbon atoms or a branched alkyl group having 3 to 6 carbon atoms. X represents a chlorine atom, a bromine atom or an iodine atom.

The above linear alkyl group having 1 to 3 carbon atoms includes methyl, ethyl and n-propyl. The above branched alkyl group having 3 to 6 carbon atoms includes, for example, isopropyl, isobutyl, sec-butyl and the like. $R^{11}$, $R^{12}$ and $R^{13}$ each are preferably a linear alkyl group having 1 to 3 carbon atoms, and they each are more preferably methyl. X is preferably a chlorine atom or a bromine atom.

In the scheme described above, both the preferred n and the preferred groups of respective $R^1$, $R^2$, $R^3$, $R^4$, $R^5$, $R^6$, $R^7$, $R^8$, $R^9$ and $R^{10}$ in dithiol (2), acetal (3), halide (4) and alcohol (5) are the same as both the preferred n and the preferred groups of $R^1$, $R^2$, $R^3$, $R^4$, $R^5$, $R^6$, $R^7$, $R^8$, $R^9$ and $R^{10}$ in the acrylic ester derivative (1) described above.

The first step to the third step described above shall be explained below in order.

First Step:

In the first step, the halide (4) is synthesized by transacetalation.

The halide (4) can readily be synthesized by reacting acetal (hereinafter referred to as acetal (3)) corresponding to the halide (4) with acid anhydride in the presence of an acid catalyst (refer to Tetrahedron, Vol. 50, No. 26, p. 7897 to 7902 (1994)).

Industrially available compounds or compounds produced by subjecting corresponding α-haloketones or α-haloaldehydes to conventional acetalization can be used as the acetal (3) used in the first step.

The specific examples of the acetal (3) include, for example, chloroacetaldehyde=dimethyl=acetal, chloroacetaldehyde=diethyl=acetal, bromoacetaldehyde=dimethyl=acetal, bromoacetaldehyde=diethyl=acetal, 1-bromo-2,2-dimethoxypropane, 1-iodo-2,2-diethoxypropane, 2-bromo-3,3-diethoxybutane, 1-chloro-2,2-dimethoxyhexane, 1-chloro-2,2-dimethoxyheptane, 1-chloro-2,2-dimethoxycyclopentane, 1-chloro-2,2-dimethoxycyclohexane, 1-bromo-2,2-dimethoxycycloheptahe and the like, but they shall not specifically be restricted to the above compounds.

The acid anhydride used in the first step includes acetic anhydride, propionic anhydride, butanoic anhydride and the like, and acetic anhydride is preferred from the viewpoints of an economical efficiency and easiness in after-treatment. A use amount of the acid anhydride falls in a range of preferably 0.5 to 3 moles, more preferably 0.7 to 2 moles per mole of the acetal (3) from the viewpoints of an economical efficiency and easiness in after-treatment.

The first step can be carried out in the presence or the absence of a solvent. The solvent shall not specifically be restricted as long as the reaction is not inhibited, and it includes, for example, aliphatic hydrocarbons such as hexane, heptane, octane and the like; aromatic hydrocarbons such as toluene, xylene, cymene and the like; halogenated hydrocarbons such as methylene chloride, dichloroethane and the like; ethers such as tetrahydrofuran (THF), diisopropyl ether and the like. They can be used alone or in a mixture of two or more kinds thereof. Further, the acid anhydride is preferably used in the form of a solvent-cum-reactant from the viewpoint of a reduction in an environmental load.

When the solvent is used, a use amount thereof falls in a range of preferably 0.1 to 10 mass, more preferably 0.1 to 5 mass per mass of the acetal (3) from the viewpoints of an economical efficiency and easiness in after-treatment.

An acid catalyst is used in the first step. The above acid catalyst includes, for example, carboxylic acids such as acetic acid, propionic acid, benzoic acid and the like; sulfonic acids such as p-toluenesulfonic acid, methanesulfonic acid and the like; mineral acids such as sulfuric acid, hydrochloric acid, phosphoric acid and the like. A use amount of the acid catalyst falls in a range of preferably 0.0001 to 0.1 mole, more preferably 0.0001 to 0.05 mole per mole of the acetal (3) from the viewpoints of an economical efficiency and easiness in after-treatment.

A reaction temperature in the first step is varied depending on the kinds of the acetal (3) and the acid catalyst, and it falls in a range of preferably 0 to 100° C., more preferably 10 to 70° C.

A pressure in the first step is varied depending on the kinds of the acetal (3), the acid catalyst, the acid anhydride and the solvent, and it can be carried out under either atmospheric pressure or reduced pressure.

The reaction in the first step can be terminated by neutralizing the acid catalyst or removing the acid catalyst from the reaction system.

The neutralizer includes, for example, alkali metal hydroxides such as sodium hydroxide, potassium hydroxide and the like; alkali metal carbonates such as sodium carbonate, potassium carbonate and the like; alkali metal hydrogencarbonates such as sodium hydrogencarbonate, potassium hydrogencarbonate and the like; tertiary amines such as triethylamine, tributylamine and the like; nitrogen-containing alicyclic aromatic hydrocarbons such as pyridine and the like. Among them, the alkaline metal hydrogencarbonates are preferred, and sodium hydrogencarbonate is more preferred.

When the neutralizer is used, a use amount thereof falls in a range of preferably 1 to 3 equivalents based on the acid catalyst from the viewpoints of an economical efficiency and easiness in after-treatment. The solvent described above which can be for the reaction may be added for dilution before adding the neutralizer.

A method for terminating the reaction by removing the acid catalyst from the reaction system includes, for example, a method in which a reaction solution under reaction is suitably diluted with a suited reaction solvent and in which it is then washed with water or an alkaline aqueous solution. The solvent includes preferably the same ones as the solvents described above which can be used in the reaction of the first step. When the solvent is used for dilution, a use amount thereof falls in a range of preferably 0.1 to 10 mass, more preferably 0.1 to 5 mass per mass of a whole mass of the reaction solution from the viewpoints of an economical efficiency and easiness in after-treatment.

Also, the basic substance in the alkaline aqueous solution includes, for example, inorganic bases such as sodium hydroxide, potassium hydroxide, sodium carbonate, sodium hydrogencarbonate, potassium carbonate, potassium hydrogencarbonate and the like. When the alkaline aqueous solution is used, a use amount of the basic substance falls in a range of preferably 0.1 to 3 equivalents based on the acid catalyst from the viewpoints of an economical efficiency and easiness in after-treatment.

The product obtained in the first step can be elevated in a purity by conventional separation/refinement for organic compounds such as solvent extraction, distillation, column chromatography, recrystallization and the like.

Second Step:

The second step comprises a step in which the dithiol (2) is reacted with the base (hereinafter referred to as a second step-1), a step in which the halide (4) is added to the reaction solution obtained in the second step-1 to obtain the alcohol (5) (hereinafter referred to as a second step-2), a step in which the ester (6) by-produced in the second step-2 is hydrolyzed if necessary (hereinafter referred to as a second step-3) and an after-treating step.

The specific examples of the alcohol (5) obtained in the second step include, for example, alcohols represented by the following formulas, but they shall not specifically be restricted to these compounds.

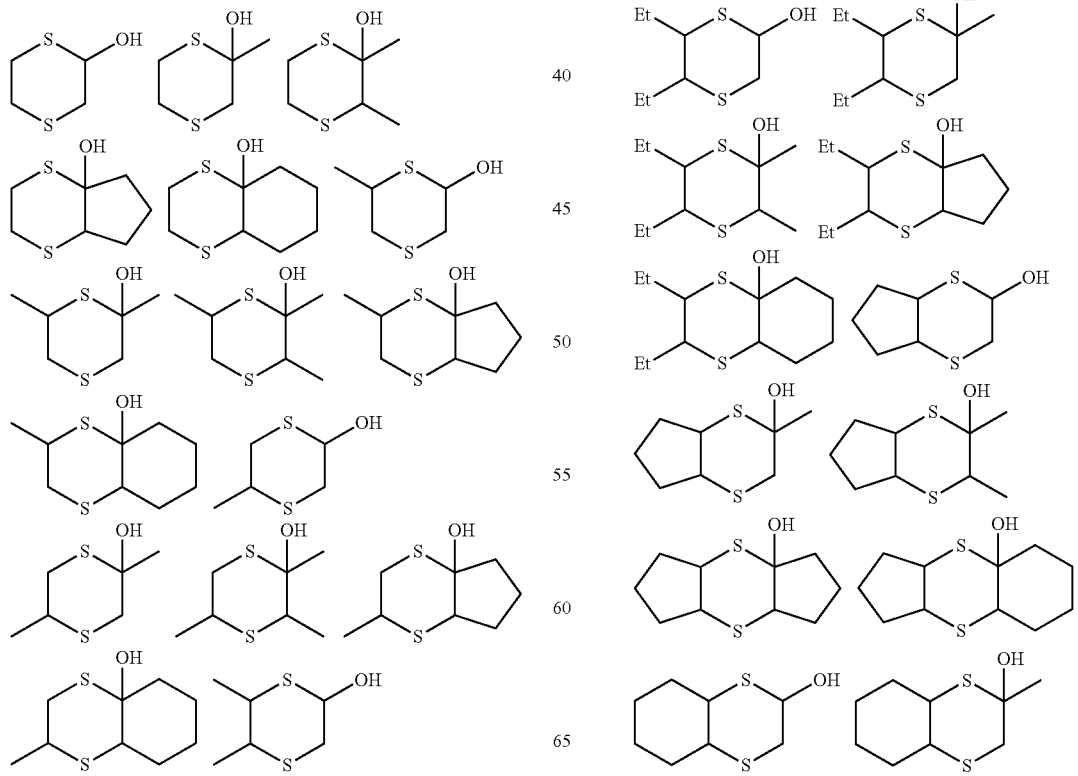

-continued

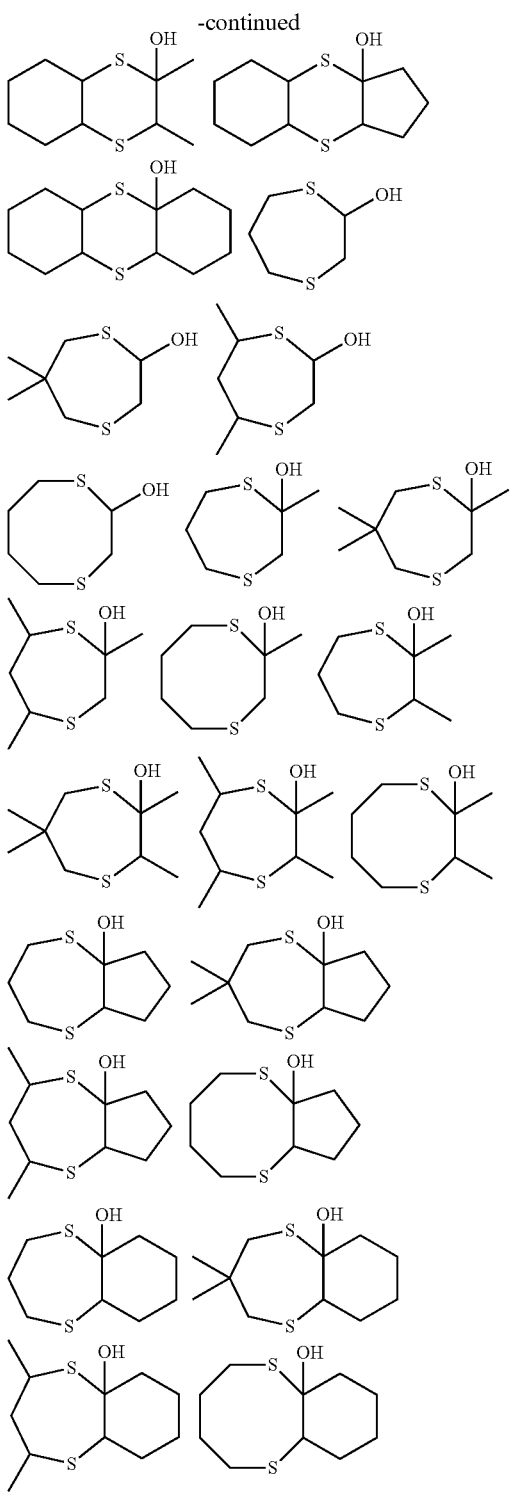

The second step can be referred to a method described in "Gazzeta Chimica Italiana, Vol. 127, No. 1, p. 11 to 17 (1997)". It is described in the above document that lithium hydride used as the base provides the best result, but the examples of the base other than it are not described. Use of lithium hydride provides no any problems in a small amount scale in a laboratory, but problems are involved in an availability and a handling thereof in an industrial scale, and therefore the present inventors have investigated the step by using sodium hydride which can usually be used. As a result thereof, a selectivity of the targeted alcohol (5) is lower when sodium hydride is used than when lithium hydride is used, and they have found that a cause thereof is attributable to a larger production amount of the ester (6) as compared with a case where lithium hydride is used. Then, they have considered that if the above ester (6) can be hydrolyzed and converted into the targeted alcohol (5), the above method shall be a useful method, and therefore they have intensely investigated the method to find that the ester (6) can readily be converted into the targeted alcohol (5) by carrying out hydrolysis in an alkaline aqueous solution, and thus they have completed the present invention.

Second Step-1:

The second step-1 is a step in which the dithiol (2) is reacted with the base to produce a salt of the dithiol (2).

The dithiol (2) used in the second step-1 includes, for example, 1,2-ethanedithiol, 1,3-propanedithiol, 1,4-butanedithiol, 2,3-butanedithiol, 2,3-dimethyl-2,3-butanedithiol, 1,2-propanedithiol, 2-methyl-1,2-propanedithiol, 2-methyl-2,3-butanedithiol, 3,4-hexanedithiol, 2,5-dimethyl-3,4-hexanedithiol, 1,2-butanedithiol, 1,2-pentanedithiol, 3,4-octanedithiol, 3,3-dimethyl-1,2-butanedithiol, 1,2-cyclopentanedithiol, 1,2-cyclohexanedithiol, 1,3-butanedithiol, 2-methyl-1,3-butanedithiol, 2,4-pentanedithiol, 2,2-dimethyl-1,3-propanedithiol, 3-methyl-1,3-butanedithiol, 2-methyl-2,4-pentanedithiol, 2-ethyl-1,3-propanedithiol, 2,4-dimethyl-2,4-pentanedithiol, 2,2-diethyl-1,3-propanedithiol, 2,4-hexanedithiol and the like, but they shall not specifically be restricted to the above compounds.

The second step-1 is carried out preferably in the presence of a solvent. The solvent shall not specifically be restricted as long as the reaction is not inhibited, and it includes, for example, dialkyl ethers such as diethyl ether, tetrahydrofuran, diisopropyl ether, t-butyl methyl ether, cyclopropyl methyl ether and the like; (poly)alkylene glycol dialkyl ethers such as 1,2-dimethoxyethane, diethylene glycol dimethyl ether, triethylene glycol dimethyl ether and the like; amides such as N,N-dimethylformamide and the like. They may be used alone or in a mixture of two or more kinds thereof. Among them, ethers (for example, dialkyl ethers and (poly)alkylene glycol dialkyl ethers) are preferred, and 1,2-dimethoxyethane is more preferred.

A use amount of the solvent falls in a range of preferably 1 to 15 mass, more preferably 3 to 10 mass per mass of the dithiol (2) from the viewpoints of an economical efficiency and easiness in after-treatment.

The base used in the second step-1 may be any of an inorganic base and an organic base. The inorganic base includes, for example, alkali metal hydrides such as sodium hydride, lithium hydride, potassium hydride and the like; alkali metal hydroxides such as sodium hydroxide, potassium hydroxide and the like; alkali metal carbonates such as sodium carbonate, potassium carbonate and the like. The organic base includes, for example, alkali metal salts of alcohols such as sodium methoxide and the like; tertiary amines such as triethylamine, N,N-dimethylaniline, tributylamine, diazabicyclo[2.2.2]octane and the like; nitrogen-containing heterocyclic aromatic compounds such as pyridine, 4-(N,N-dimethylamino)pyridine and the like. They may be used alone or in a mixture of two or more kinds thereof. Among them, alkali metal hydrides are preferred from the viewpoints of an availability, handling, a reaction yield and an economical efficiency, and sodium hydride is more preferred. A use amount of the base falls in a range of preferably 0.8 to 4 moles, more preferably 1.5 to 2.5 moles based on 1 mole of the dithiol (2) from the viewpoints of an economical efficiency and easiness in after-treatment. If a use amount of the base falls in the ranges described above, a yield of the alcohol (5) in the second step-2 is improved.

The procedure of the second step-1 shall not specifically be restricted, and when sodium hydride is used as the base, a method in which the dithiol (2) is dropwise added to a solution obtained by suspending sodium hydride in a suitable solvent is preferred.

A reaction temperature in the second step-1 is varied depending on the kinds of the dithiol (2) and the base, and it falls in a range of preferably about 0 to 100° C., more preferably 5 to 70° C. and further preferably 10 to 50° C.

A pressure in the second step-1 is varied depending on the kinds of the dithiol (2), the base and the solvent, and it can be carried out under optional pressure and is carried out preferably under atmospheric pressure.

A reaction time in the second step-1 falls in a range of preferably 0.1 to 5 hours, more preferably 0.1 to 2 hours after finishing addition of the dithiol (2). Particularly when sodium hydride is used as the base, the reaction time falls in a range of preferably 0.1 to 3 hours, more preferably 0.1 to 1.5 hour after finishing addition of the dithiol (2). When sodium hydride is used as the base, hydrogen is generated as the reaction proceeds, but if the reaction time falls in a range of 0.1 to 3 hours, hydrogen is terminated to be generated.

Second Step-2:

The second step-2 is carried out by reacting a reaction solution containing a salt of the dithiol (2) obtained in the second step-1 with the halide (4) obtained in the first step.

The procedure of the second step-2 shall not specifically be restricted and can be carried out, for example, by a method in which the halide (4) obtained in the first step is dropwise added to a reaction solution containing a salt of the dithiol (2) obtained in the second step-1.

A reaction temperature in the second step-2 is varied depending on the kinds of the dithiol (2), the base and the solvent which are used in the second step-1 and the halide (4) obtained in the first step, and it falls in a range of preferably 0 to 100° C., more preferably 10 to 80° C.

A pressure in the second step-2 is varied depending on the kinds of the dithiol (2), the base and the solvent which are used in the second step-1 and the halide (4) obtained in the first step, and it can be carried out at optional pressure and is carried out preferably at atmospheric pressure.

A reaction time in the second step-2 falls in a range of preferably 0.1 to 10 hours, more preferably 0.5 to 5 hours after finishing addition of the halide (4) obtained in the first step. Particularly when sodium hydride is used as the base, the reaction time falls in a range of preferably 0.1 to 8 hours, more preferably 0.5 to 4 hour after finishing addition of the halide (4) obtained in the first step. If the reaction time falls in the above ranges, a conversion of the halide (4) obtained in the first step is usually 98% or more.

In the second step-2, the ester (6) is by-produced together with the targeted alcohol (5). The above ester (6) is by-produced in a proportion of the alcohol (5): the ester (6)=10:90 to 70:30 (area ratio) when it is analyzed by gas chromatography.

Second Step-3:

The second step-3 is a step in which after finishing the reaction in the second step-2, the ester (6) by-produced is suitably hydrolyzed to enhance a yield of the targeted alcohol (5). The second step-3 is carried out by adding water or an alkali aqueous solution to the reaction solution obtained in the second step-2 and stirring the mixture.

A number of moles of the base used in the second step-1 exceeds a number of moles of the halide used in the second step-2 in many cases, and therefore when water is used in the second step-3, a pH of the solution to which water is added falls in a range of approximately 10 to 14 (alkaline) and shows a range of 11 to 13 in more cases. An amount of water added is not only a theoretical amount required for hydrolyzing the ester (6) by-produced but also, considering an after-treating step, falls in a range of preferably 0.1 to 5 mass, more preferably 0.1 to 1 mass per mass of the whole solution in the second step-2.

When an alkali aqueous solution is used, a basic substance contained in the above alkali aqueous solution is preferably an inorganic salt, and the inorganic salt includes, for example, alkali metal hydroxides such as sodium hydroxide, potassium hydroxide and the like; alkali metal carbonates such as sodium carbonate, potassium carbonate and the like; and alkali metal hydrogencarbonates such as sodium hydrogencarbonate, potassium hydrogencarbonate and the like.

A use amount of the basic substance falls in a range of preferably 0.1 to 5 moles, more preferably 0.5 to 3 moles based on 1 mole of the ester (6) from the viewpoints of an economical efficiency and easiness in after-treatment. A concentration of the alkali aqueous solution shall not specifically be restricted and can be used in a range of usually 0.01 to 20% by mass.

A method in which the alkali aqueous solution or merely the basic substance is added, if necessary, after adding water in the second step-3 can be employed as well.

The temperature in adding water or the alkali aqueous solution in the second step-3 falls in a range of preferably 0 to 100° C., more preferably 10 to 80° C. and further preferably 20 to 50° C. The temperature in the middle of mixing after adding water or the alkali aqueous solution shall not specifically be restricted and falls in a range of preferably 20 to 100° C., and it is more preferably 50 to 100° C. from the viewpoint of capable of shortening the reaction time.

A pressure in the second step-3 is varied depending on the kinds of the dithiol (2), the base and the solvent which are used in the second step-1 and the halide (4) obtained in the first step, and it can be carried out under optional pressure and is carried out preferably under atmospheric pressure.

A reaction time in the second step-3 shall not specifically be restricted, and it is desirable to follow up changes of the alcohol (5) and the ester (6) with the passage of time by gas chromatography and the like to stop mixing at the point of time when a yield of the alcohol (5) is not elevated. Mixing may be continued over the above point of time, but a yield of the alcohol (5) tends to be gradually reduced. When a yield of the alcohol (5) reaches a maximum point, a ratio of the alcohol (5) to the ester (6) which is analyzed by gas chromatography falls in a range of the alcohol (5): the ester (6)=70:30 to 99:1 (area ratio).

The hydrolysis in the second step-3 can be terminated by neutralizing the excessive base. The neutralizer includes mineral acids such as sulfuric acid, hydrochloric acid, phosphoric acid and the like. The above acids diluted to a suitable concentration by water may be used. A targeted pH thereof in neutralizing falls in a range of preferably 7 to 8.

The targeted alcohol (5) contained in the solution after finishing the hydrolysis in the second step-3 can be elevated in a purity by conventional separation/refinement for organic compounds such as solvent extraction, distillation, column chromatography, recrystallization and the like.

Third Step:

The third step is a step in which a polymerizable group is introduced into the alcohol (5) obtained in the second step.

A method for introducing the polymerizable group into the alcohol (5) shall not specifically be restricted, and it is carried out by reacting the alcohol (5) with a compound (hereinafter referred to as a polymerizable group-introducing agent) represented by a formula $CH_2=CR^1COX^1$, a formula $(CH_2=CR^1CO)_2O$, a formula $CH_2=CR^1COOC(=O)R^{14}$ or a formula $CH_2=CR^1COOSO_2R^{15}$ in the presence of a basic substance.

In the polymerizable group-introducing agent described above, all of $R^1$ are the same as $R^1$ in the acrylic ester derivative (1) described above, and the preferred groups are the same as well. $X^1$ represents a chlorine atom, a bromine atom or an iodine atom. $R^{14}$ represents t-butyl or 2,4,6-trichlorophenyl. $R^{15}$ represents methyl or p-tolyl.

The specific examples of the polymerizable group-introducing agent represented by the formula $CH_2=CR^1COX^1$ include, for example, acrylic chloride, methacrylic chloride, 2-trifluoromethylacrylic chloride and the like.

The specific examples of the polymerizable group-introducing agent represented by the formula $(CH_2=CR^1CO)_2O$ include, for example, acrylic anhydride, methacrylic anhydride, 2-trifluoromethylacrylic anhydride and the like.

The specific examples of the polymerizable group-introducing agent represented by the formula $CH_2=CR^1COOC(=O)R^{14}$ include, for example, acrylic pivalic anhydride, acrylic 2,4,6-trichlorobenzoic anhydride, methacrylic pivalic anhydride, methacrylic 2,4,6-trichlorobenzoic anhydride, 2-trifluoromethylacrylic pivalic anhydride, 2-trifluoromethylacrylic 2,4,6-trichlorobenzoic anhydride and the like.

The specific examples of the polymerizable group-introducing agent represented by the formula $CH_2=CR^1COOSO_2R^{15}$ include, for example, acrylic methanesulfonic anhydride, acrylic p-toluenesulfonic anhydride, methacrylic methanesulfonic anhydride, methacrylic p-toluenesulfonic anhydride, 2-trifluoromethylacrylic methanesulfonic anhydride, 2-trifluoromethylacrylic p-toluenesulfonic anhydride and the like.

Among them, the polymerizable group-introducing agents represented by the formula $CH_2=CR^1COX^1$ are preferred, and acrylic chloride and methacrylic chloride are more preferred.

A use amount of the polymerizable group-introducing agent falls in a range of preferably 0.8 to 5 moles, more preferably 0.8 to 3 moles based on 1 mole of the alcohol (5) from the viewpoints of an economical efficiency and easiness in after-treatment.

Any of an inorganic base and an organic base can be used for the basic substance used in the third step. The inorganic base includes, for example, alkali metal hydrides such as sodium hydride, potassium hydride and the like; alkali metal hydroxides such as sodium hydroxide, potassium hydroxide and the like; and alkali metal carbonates such as sodium carbonate, potassium carbonate and the like. The organic base includes, for example, tertiary amines such as triethylamine, tributylamine, N,N-dimethylaniline, diazabicyclo[2.2.2]octane and the like; and nitrogen-containing heterocyclic aromatic compounds such as pyridine, 4-(N,N-dimethylamino) pyridine and the like. They may be used alone or in a mixture of two or more kinds thereof. Among them, the tertiary amines are preferred.

A use amount of the basic substance falls in a range of preferably 0.8 to 5 moles, more preferably 0.8 to 3 moles based on 1 mole of the alcohol (5) from the viewpoints of an economical efficiency and easiness in after-treatment.

The third step can be carried out in the presence or the absence of a solvent. The solvent shall not specifically be restricted as long as the reaction is not inhibited, and it includes, for example, ethers such as diethyl ether, diisopropyl ether, tetrahydrofuran and the like; aliphatic hydrocarbons such as hexane, heptane, octane and the like; halogenated hydrocarbons such as methylene chloride, 1,2-dichloroethane and the like; aromatic hydrocarbons such as toluene, xylene, cymene and the like; N,N-dimethylformamide; dimethylsulfoxide and the like. They may be used alone or in a mixture of two or more kinds thereof.

When the solvent is used, a use amount thereof shall not specifically be restricted and falls usually in a range of preferably 0.1 to 20 parts by mass, more preferably 0.1 to 10 parts by mass based on 1 part by mass of the alcohol (5).

The third step is carried out in a range of preferably −80 to 100° C., more preferably −50 to 80° C. and further preferably −20 to 40° C. The reaction time is varied depending on the kinds and the use amounts of the alcohol (5) and the polymerizable group-introducing agent, the kind and the use amount of the basic substance, the kind and the use amount of the solvent and the reaction temperature, and it falls usually in a range of 10 minutes to 10 hours.

In the third step, the reaction can be terminated by adding water and/or alcohol. Such alcohol includes, for example, methanol, ethanol, n-propanol, i-propanol and the like.

A use amount of water and/or alcohol is preferably 1 mole or more based on excess 1 mole of the polymerizable group-introducing agent to the alcohol (5) from the viewpoints of completely decomposing the unreacted polymerizable group-introducing agent and inhibiting by-products.

The acrylic ester derivative (1) obtained via the above third step is preferably separated and refined, if necessary, by a conventional method. For example, the reaction mixture is washed with water and then concentrated, and a purity thereof can be elevated by a conventional method used for separating and refining organic compounds, such as distillation, column chromatography or recrystallization.

Further, the acrylic ester derivative (1) obtained can be decreased, if necessary, in a metal content by chelate agent treatment by nitrilotriacetic acid, ethylenediaminetetraacetic acid and the like or metal-removing filter treatment by Zeta Plus (trade name, manufactured by Cuno K.K.) and Protego (trade name, manufactured by Nihon Microlis K.K.).

Polymer (8):

A polymer (hereinafter referred to as a polymer (8)) is prepared by polymerizing a raw material containing at least the acrylic ester derivative (1), and it can be used as a component for a photoresist composition.

The polymer prepared by polymerizing the acrylic ester derivative (1) is a polymer prepared by homopolymerizing the acrylic ester derivative (1) or a copolymer prepared by copolymerizing the acrylic ester derivative (1) with other polymerizable compounds, and it has a structural unit based on the acrylic ester derivative (1). Usually, a content of the structural unit based on the acrylic ester derivative (1) in the polymer (8) shall not specifically be restricted and falls in a range of preferably 10 to 90 mole %, more preferably 20 to 80 mole % from the viewpoints of a solubility to a developer for a photoresist composition described later, a heat stability and a reduction in LWR. The specific examples of the structural unit based on the acrylic ester derivative (1) include units represented by the following formulas (1'-a) to (1'-x), but they shall not be restricted to these units.

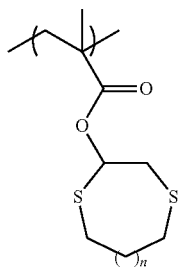 (1'-a)
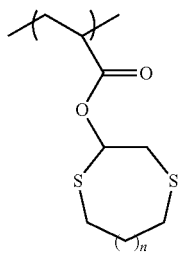 (1'-b)
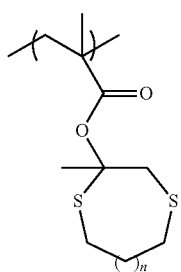 (1'-c)
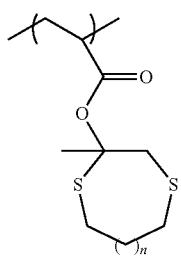 (1'-d)
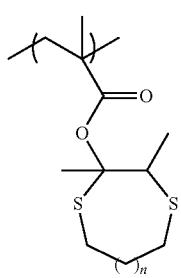 (1'-e)
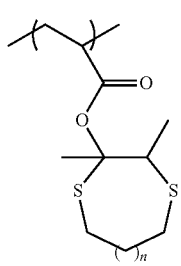 (1'-f)
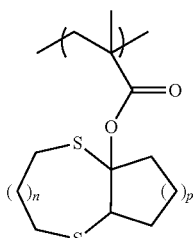 (1'-g)
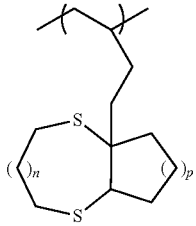 (1'-h)
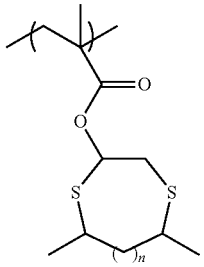 (1'-i)
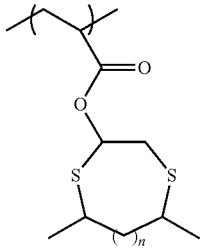 (1'-j)
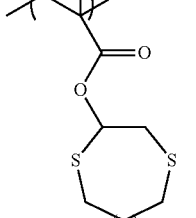 (1'-k)
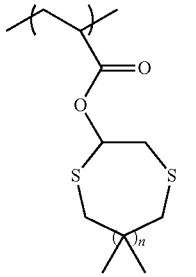 (1'-l)

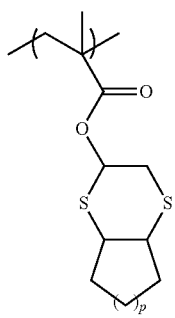 (1'-m)
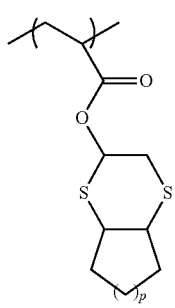 (1'-n)
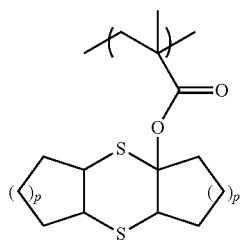 (1'-o)
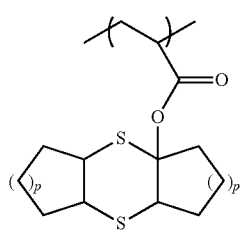 (1'-p)
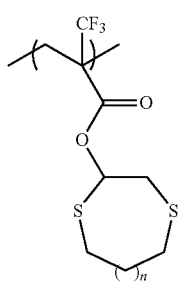 (1'-q)
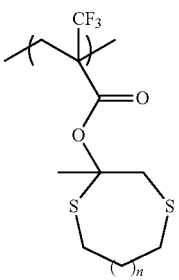 (1'-r)
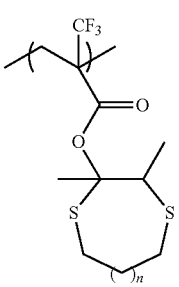 (1'-s)
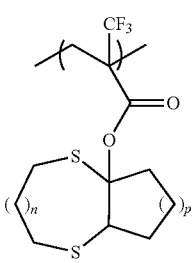 (1'-t)
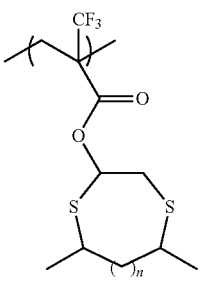 (1'-u)
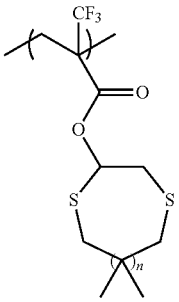 (1'-v)

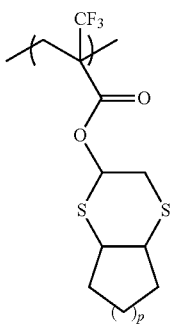
(1'-w)

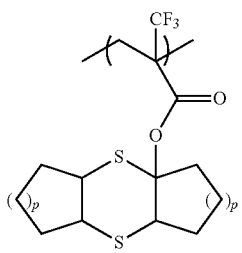
(1'-x)

The specific examples of the other polymerizable compounds (hereinafter referred to as a copolymerization monomer (7)) which can be copolymerized with the acrylic ester derivative (1) include, for example, compounds (I) to (IX) represented by the following chemical formulas:

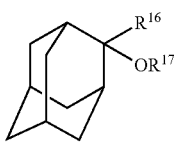
(I)

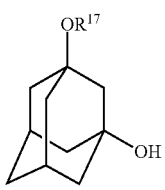
(II)

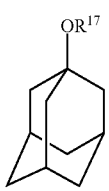
(III)

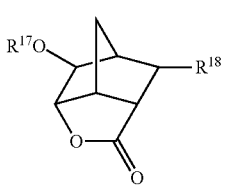
(IV)

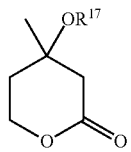
(V)

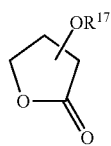
(VI)

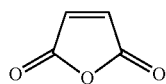
(VII)

(VIII)

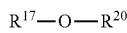

$R^{17}-O-R^{20}$ (IX)

(wherein $R^{16}$ represents a hydrogen atom or an alkyl group having 1 to 3 carbon atoms; $R^{17}$ represents a polymerizable group; Rn represents a hydrogen atom or —$COOR^{19}$, and $R^{19}$ represents an alkyl group having 1 to 3 carbon atoms; and $R^{20}$ represents an alkyl group or a cycloalkyl group in which a carbon atom forming a ring may be substituted with an oxygen atom), but they shall not specifically be restricted to these compounds.

In the copolymerization monomer (7), the alkyl group having 1 to 3 carbon atoms each represented independently by $R^{16}$ and $R^{19}$ includes methyl, ethyl, n-propyl and isopropyl. The alkyl group represented by $R^{20}$ includes, for example, alkyl groups having 1 to 8 carbon atoms such as methyl, ethyl, n-propyl, isopropyl, n-butyl, isobutyl, s-butyl, t-butyl and the like. The cycloalkyl group represented by $R^{20}$ in which a carbon atom forming a ring may be substituted with an oxygen atom includes cyclopentyl, cyclohexyl, 1-methylcyclohexyl, cyclooctyl, tetrahydropyran-2-yl, 4-methyltetrahydropyran-4-yl and the like. The polymerizable group represented by $R^{17}$ includes, for example, acryloyl, methacryloyl, 2-trifluoromethylacryloyl, vinyl, crotonoyl and the like.

$R^{16}$ is preferably a hydrogen atom, methyl, ethyl and isopropyl. $R^{17}$ is preferably acryloyl and methacryloyl. $R^{18}$ is preferably a hydrogen atom. $R^{20}$ is preferably an alkyl group having 1 to 8 carbon atoms.

The other polymerizable compounds which can be copolymerized with the acrylic ester derivative (1) are preferably the compounds (I), (II), (IV), (V), (VI) and (IX), more preferably the compounds (II), (IV) and (VI).

Production Process for the Polymer (8):

The polymer (8) can be produced by radical polymerization according to a conventional method. In particular, living radical polymerization can be listed as a method for synthesizing a polymer having a narrow molecular weight distribution. In a conventional radical polymerization method, at least one of the acrylic ester derivatives (1) according to necessity and at least one of the copolymerization monomers (7) according to necessity are polymerized in the presence of a radical initiator, a solvent and, if necessary, a chain transfer agent.

The above radical polymerization method shall be explained below.

A method for carrying out the radical polymerization shall not specifically be restricted, and conventional methods used in producing, for example, acrylic polymer, such as a solution polymerization method, an emulsion polymerization method, a suspension polymerization method, a bulk polymerization method and the like can be used.

The radical initiator includes, for example, hydroperoxides such as t-butyl hydroperoxide, cumene hydroperoxide and the like; dialkyl peroxides such as di-t-butyl peroxide, t-butyl-α-cumyl peroxide, di-α-cumyl peroxide and the like; diacyl peroxides such as benzoyl peroxide, diisobutyryl peroxide and the like; and azo compounds such as 2,2'-azobisisobutyronitrile, dimethyl-2,2'-azobisisobutylate and the like.

A use amount of the radical initiator can suitably be selected according to the polymerization conditions such as the kinds and the use amounts of the acrylic ester derivative (1), the copolymerization monomer (7), the chain transfer agent and the solvent which are used for the polymerization reaction and the polymerization temperature and the like, and it falls usually in a range of preferably 0.005 to 0.2 mole, more preferably 0.01 to 0.15 mole based on 1 mole of the whole polymerizable compounds (showing a total amount of the acrylic ester derivative (1) and the copolymerization monomer (7), and hereinafter the same shall apply).

The chain transfer agent includes, for example, thiol compounds such as dodecanethiol, mercaptoethanol, mercaptopropanol, mercaptoacetic acid, mercaptopropionic acid and the like. They may be used alone or in a mixture of two or more kinds thereof.

When the chain transfer agent is used, a use amount thereof falls in a range of usually 0.005 to 0.2 mole, preferably 0.01 to 0.15 mole based on 1 mole of the whole polymerizable compounds.

The radical polymerization is carried out usually in the presence of a solvent. The solvent shall not specifically be restricted as long as the reaction is not inhibited, and it includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like. They may be used alone or in a mixture of two or more kinds thereof.

A use amount of the solvent falls in a range of usually 0.5 to 20 parts by mass based on 1 part by mass of the whole polymerizable compounds, and it falls in a range of preferably 1 to 10 parts by mass from the viewpoint of an economical efficiency.

A reaction temperature in the radical polymerization falls usually in a range of preferably 40 to 150° C., and it falls in a range of more preferably 60 to 120° C. from the viewpoint of a stability of the polymer (8) produced.

A reaction time in the radical polymerization is varied according to the polymerization conditions such as the kinds and the use amounts of the acrylic ester derivative (1), the copolymerization monomer (7), the chain transfer agent and the solvent, the polymerization temperature and the like, and it falls usually in a range of preferably 30 minutes to 48 hours, more preferably 1 hour to 24 hours.

The polymer (8) thus obtained can be isolated by an ordinary operation such as reprecipitation.

A solvent used in the operation of the reprecipitation described above includes, for example, aliphatic hydrocarbons such as pentane, hexane and the like; alicyclic hydrocarbons such as cyclohexane and the like; aromatic hydrocarbons such as benzene, xylene and the like; halogenated hydrocarbons such as methylene chloride, chloroform, chlorobenzene, dichlorobenzene and the like; nitrated hydrocarbons such as nitromethane and the like; nitriles such as acetonitrile, benzonitrile and the like; ethers such as diethyl ether, diisopropyl ether, tetrahydrofuran, 1,4-dioxane and the like; ketones such as acetone, methyl ethyl ketone and the like; carboxylic acids such as acetic acid and the like; esters such as ethyl acetate, butyl acetate and the like; carbonates such as dimethyl carbonate, diethyl carbonate, ethylene carbonate and the like; alcohols such as methanol, ethanol, propanol, isopropanol, butanol and the like; and water. They may be used alone or in a mixture of two or more kinds thereof.

A use amount of the solvent is varied depending on the kind of the polymer (8) and the kind of the solvent, and it falls usually in a range of preferably 0.5 to 100 parts by mass based on 1 part by mass of the polymer (8), and it falls in a range of more preferably 1 to 50 parts by mass from the viewpoint of an economical efficiency.

The polymer thus isolated can be dried by vacuum drying and the like.

The specific examples of the polymer (8) obtained by the method described above include, for example, polymer represented by the following schemes (8-1) to (8-96) (wherein $R^{21}$ to $R^{35}$ each represent independently a hydrogen atom, methyl or trifluoromethyl; a, b, c, d and e represent the mole ratios of the repetitive units; a+b is equal to 1, and c+d+e is equal to 1), but they shall not be restricted to these compounds.

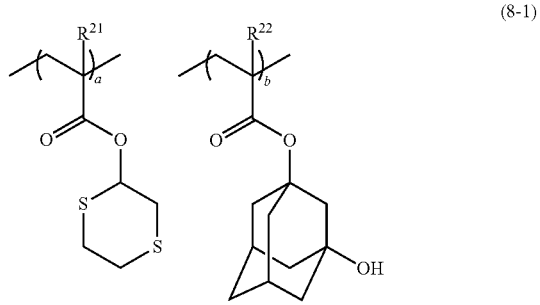

(8-1)

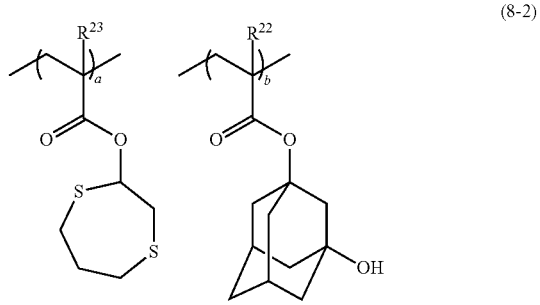

(8-2)

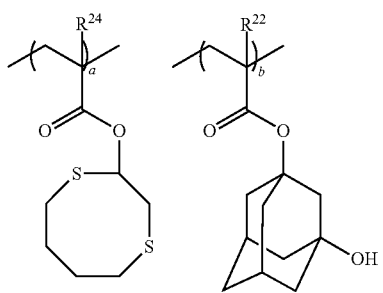 (8-3)
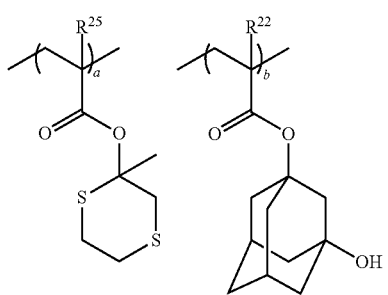 (8-4)
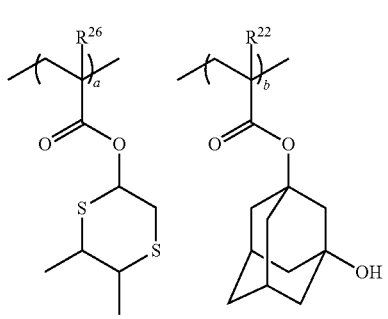 (8-5)
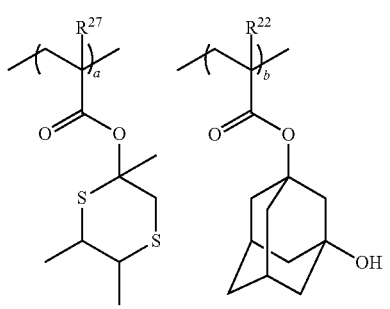 (8-6)
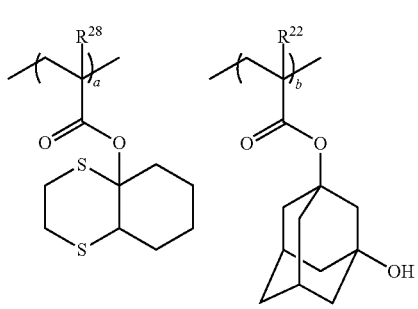 (8-7)
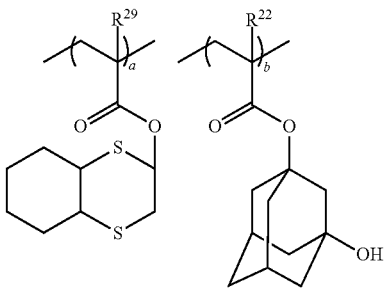 (8-8)
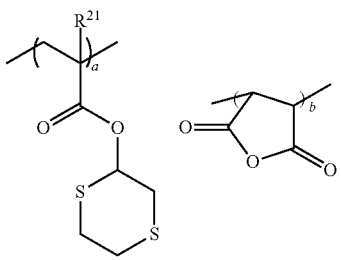 (8-9)
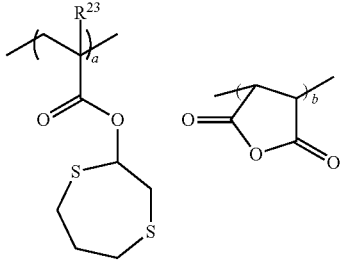 (8-10)
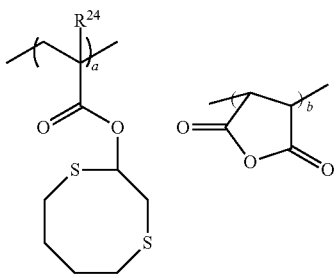 (8-11)
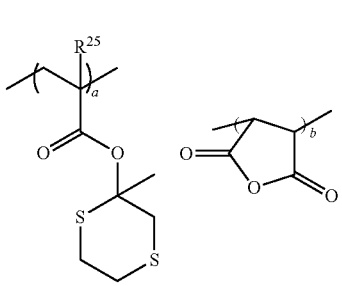 (8-12)

(8-13)
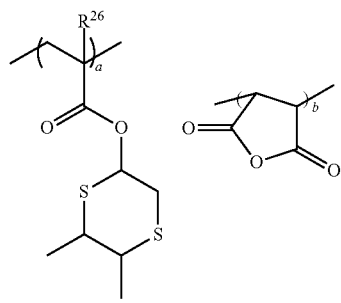
(8-14)
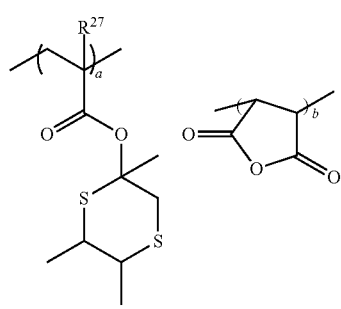
(8-15)
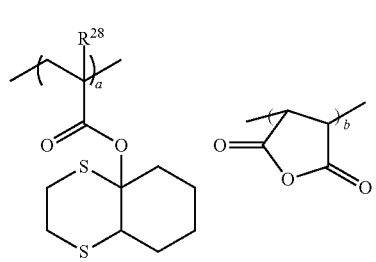
(8-16)
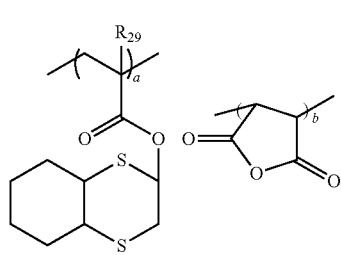
(8-17)
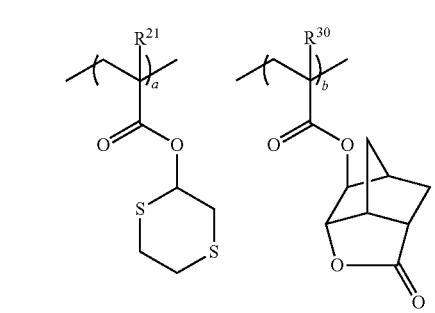
(8-18)
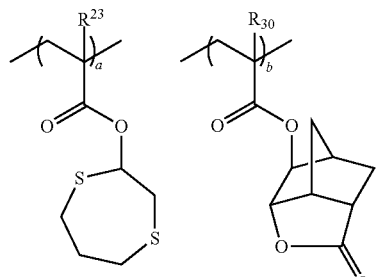
(8-19)
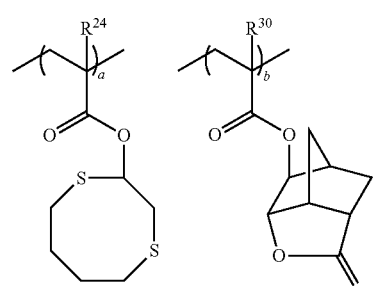
(8-20)
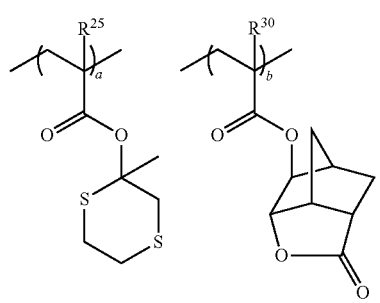
(8-21)
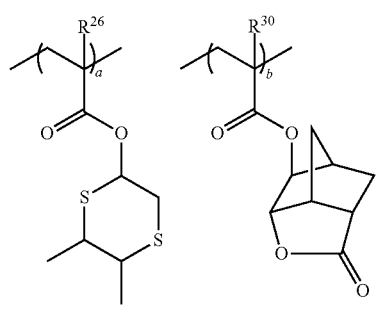
(8-22)
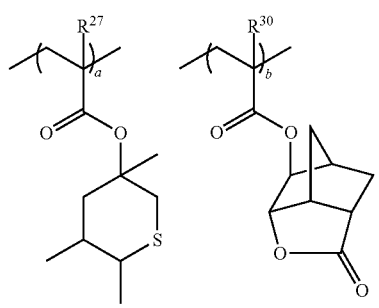

-continued

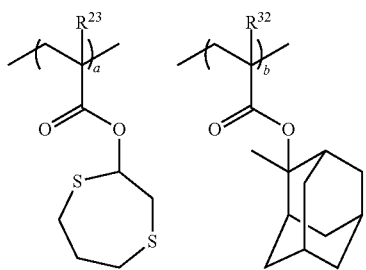 (8-34)
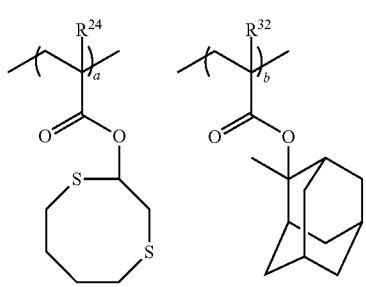 (8-35)
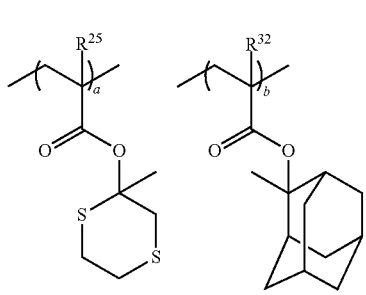 (8-36)
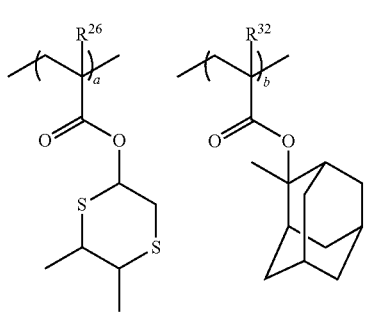 (8-37)
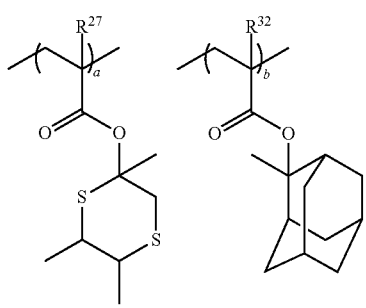 (8-38)
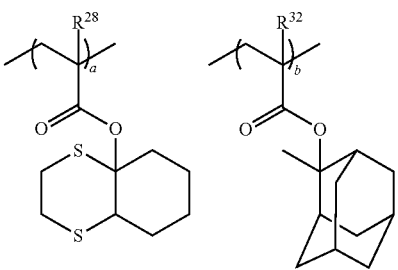 (8-39)
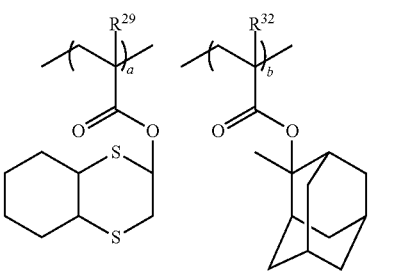 (8-40)
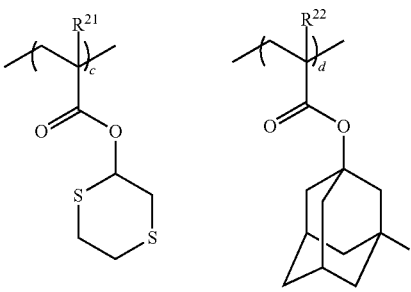 (8-41)
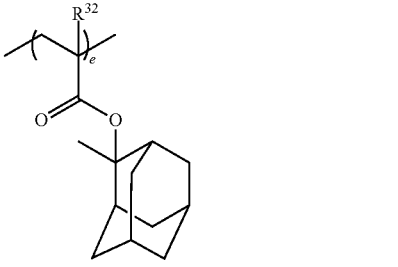 (8-37)
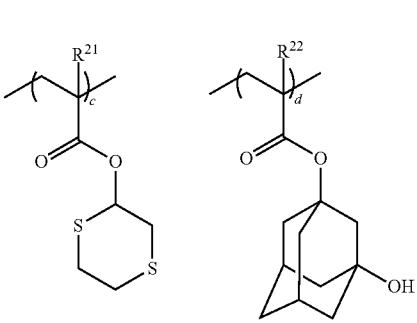 (8-42)

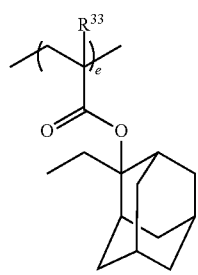
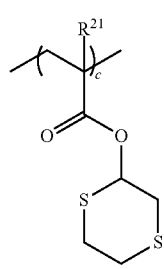
(8-43)
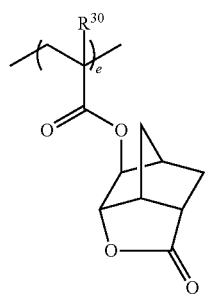
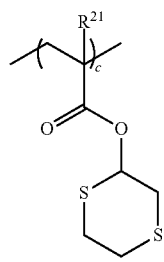
(8-44)
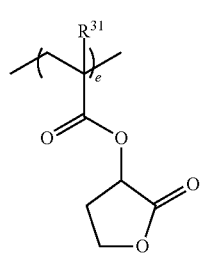
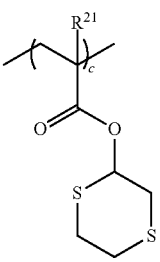 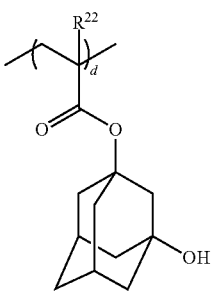
(8-45)
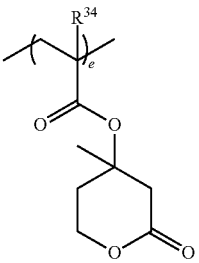
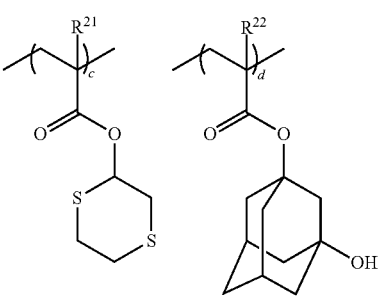
(8-46)
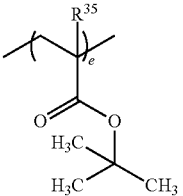
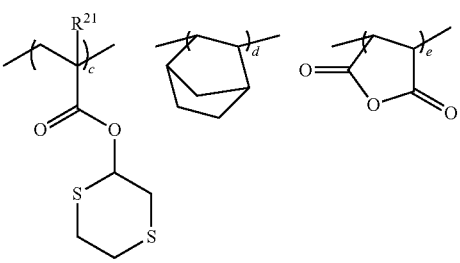
(8-47)
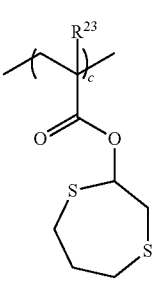 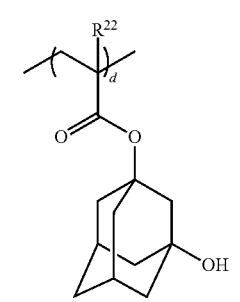
(8-48)

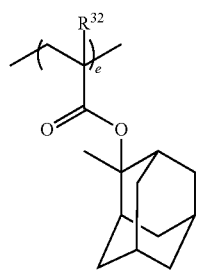
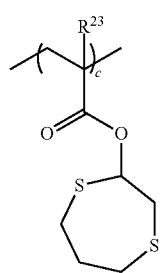
(8-49)
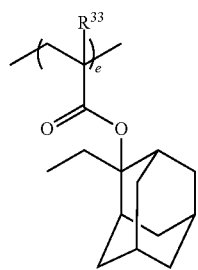
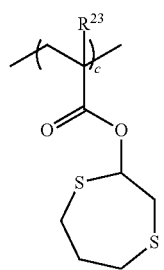
(8-50)
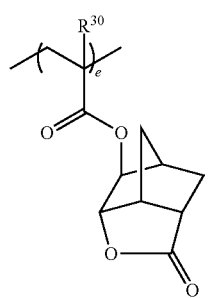
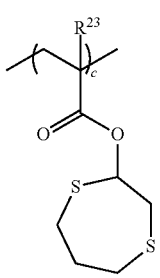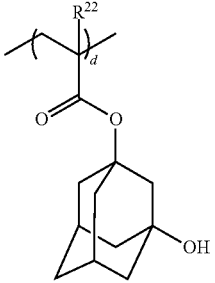
(8-51)
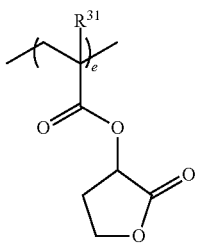
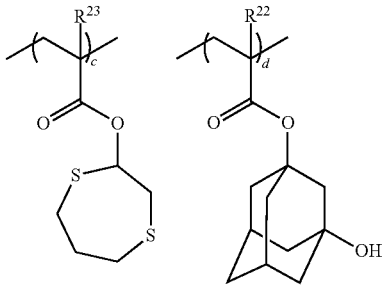
(8-52)
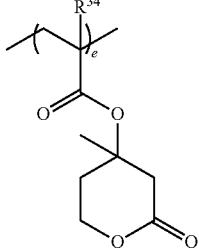
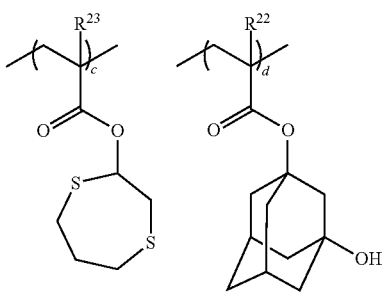
(8-53)
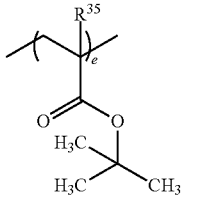

(8-54)
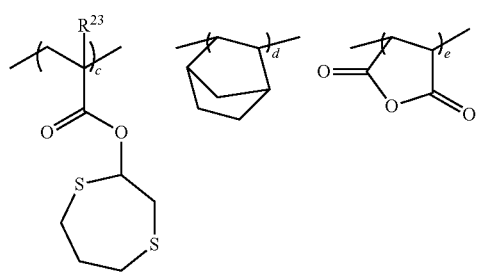
(8-55)
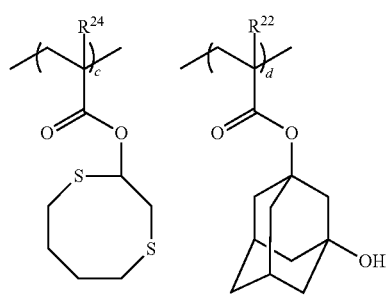
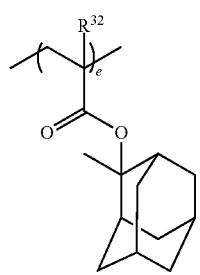
(8-56)
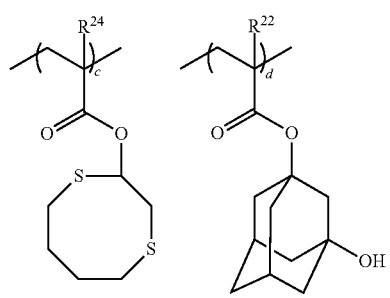
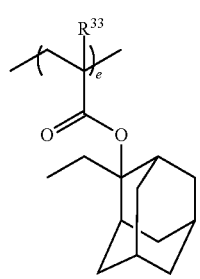
(8-57)
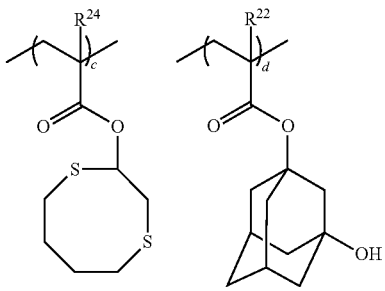
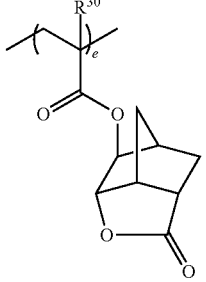
(8-58)
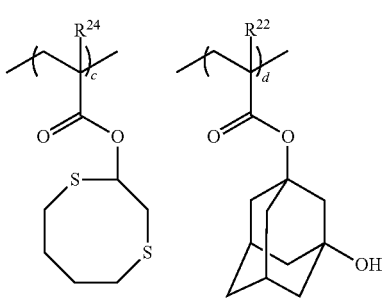
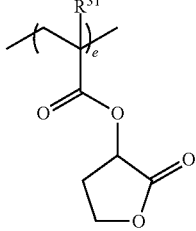
(8-59)
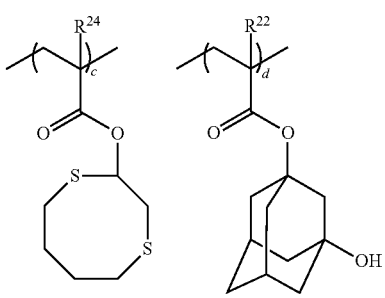
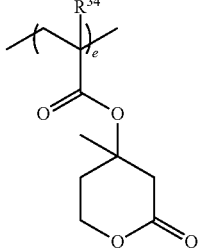

(8-60)
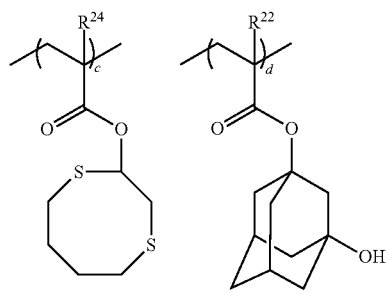
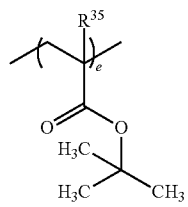
(8-61)
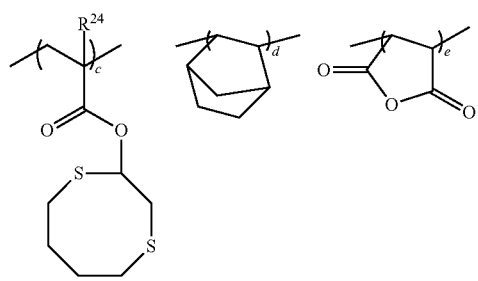
(8-62)
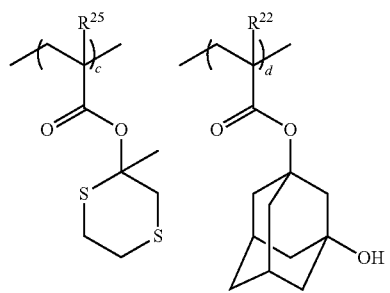
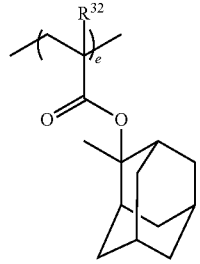
(8-63)
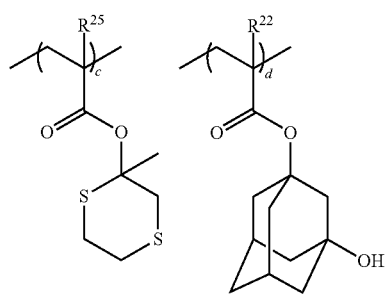
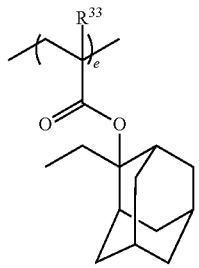
(8-64)
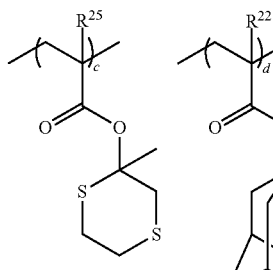
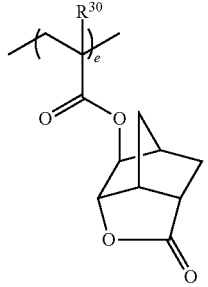
(8-65)
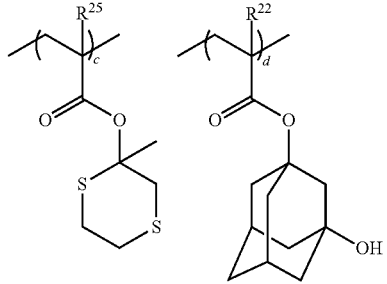
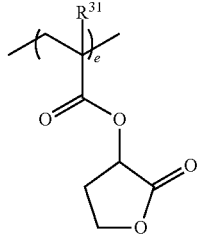
(8-66)
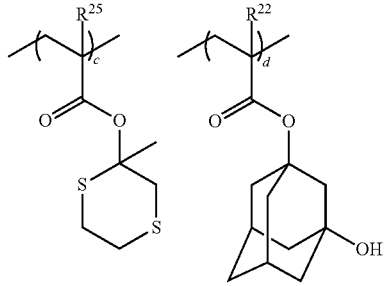

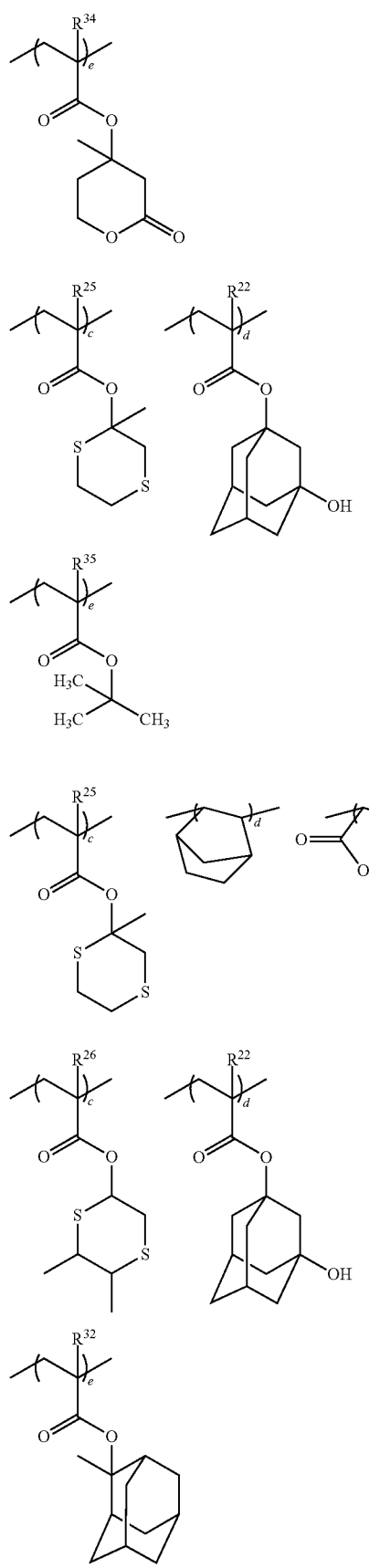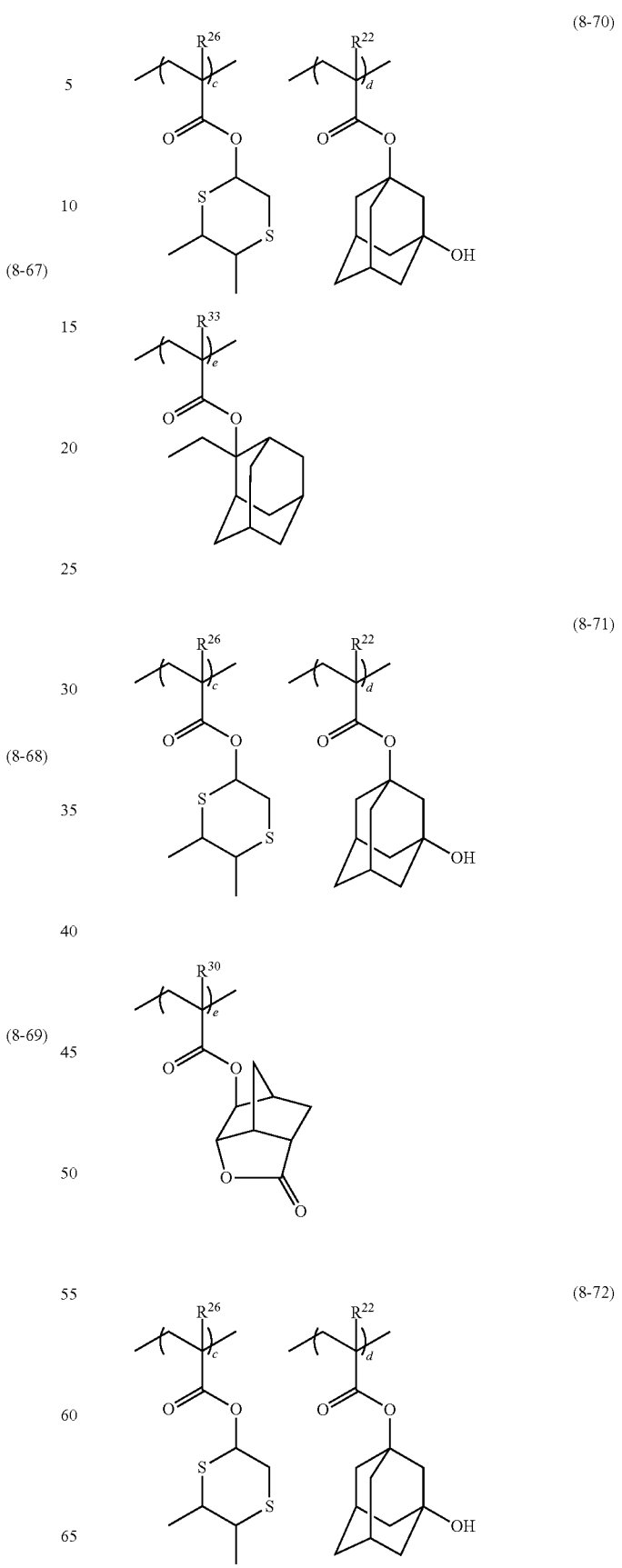

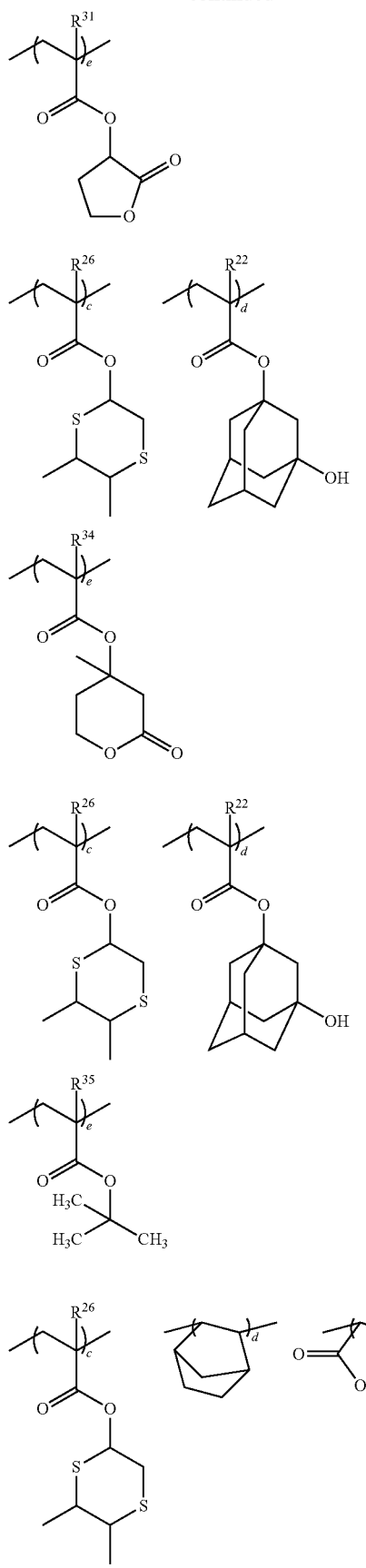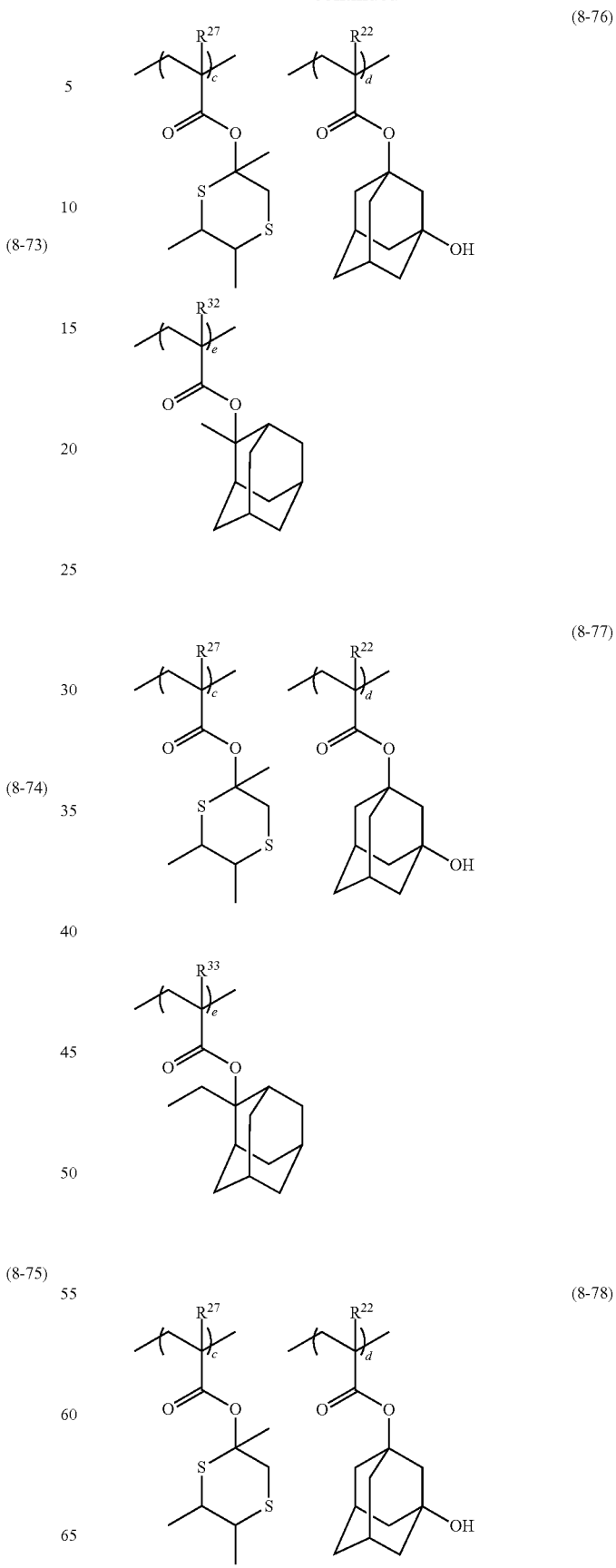

-continued
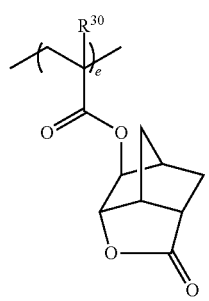
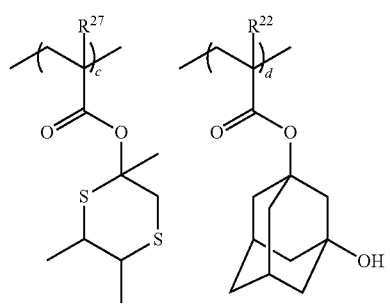
(8-79)
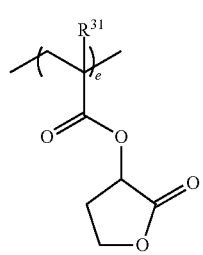
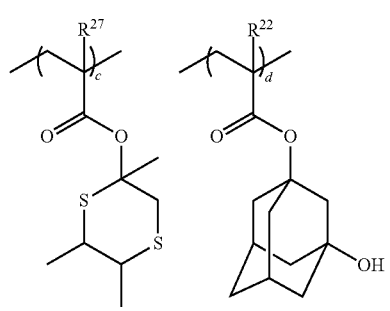
(8-80)
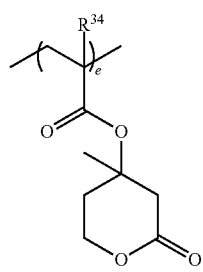
-continued
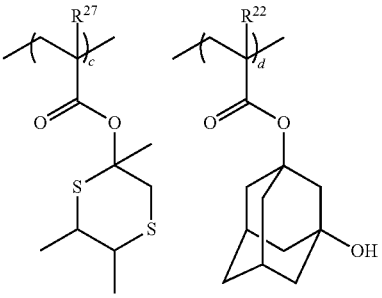
(8-81)
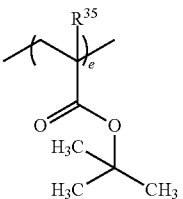
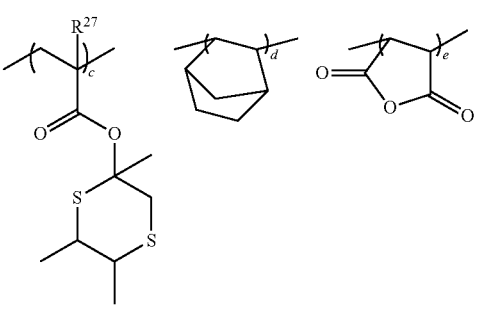
(8-82)
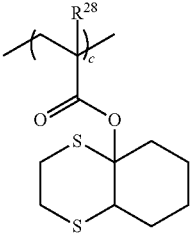
(8-83)
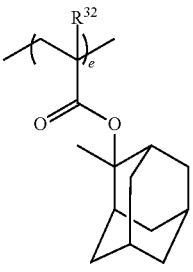

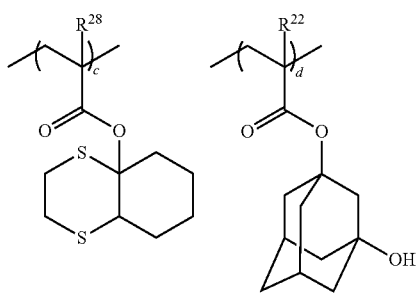
(8-84)
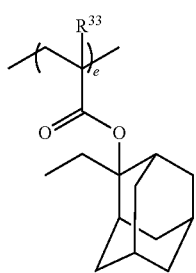
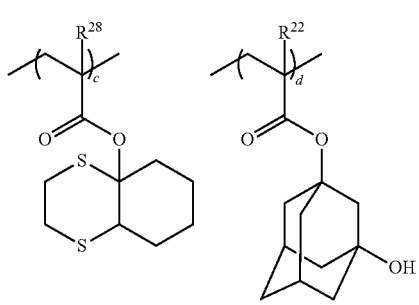
(8-85)
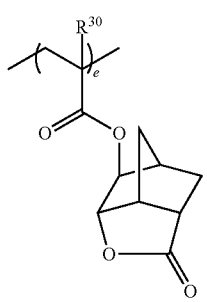
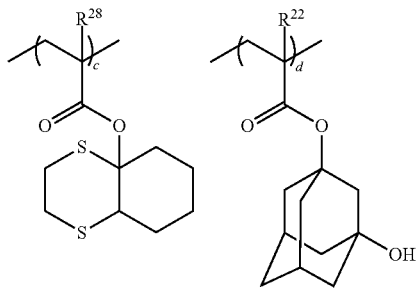
(8-86)
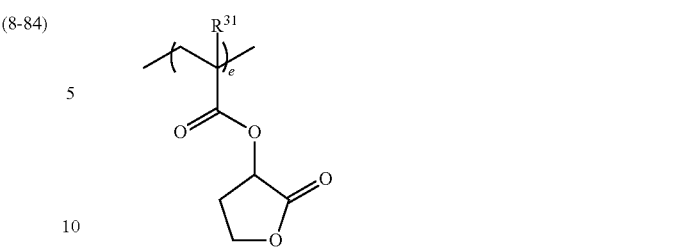
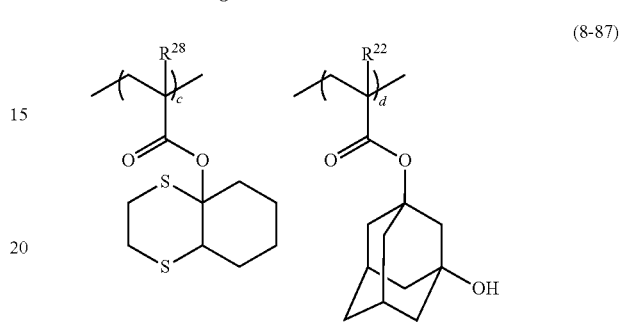
(8-87)
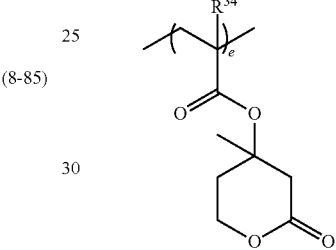
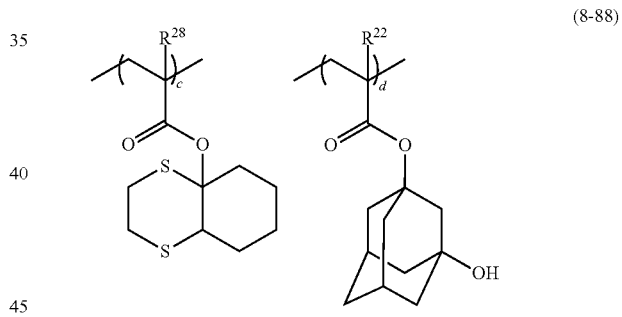
(8-88)
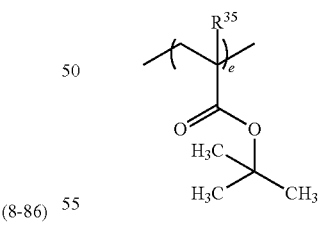
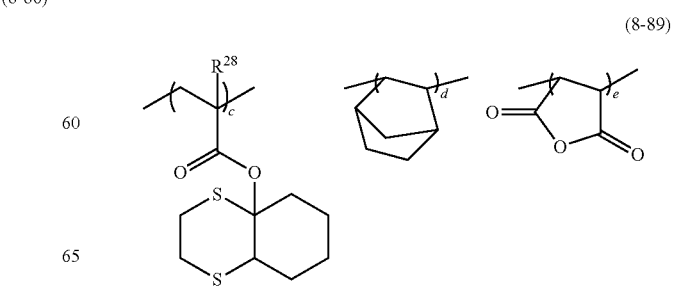
(8-89)

(8-90)
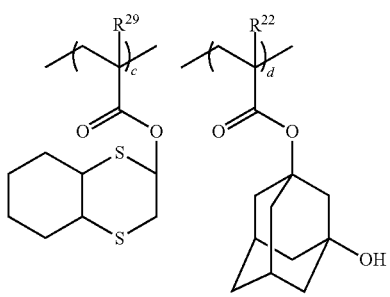
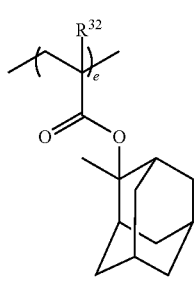
(8-91)
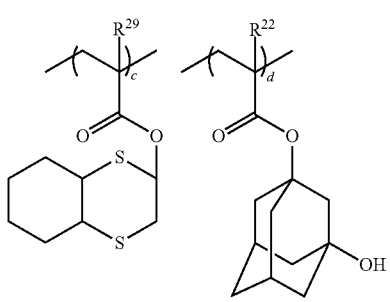
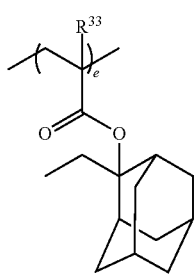
(8-92)
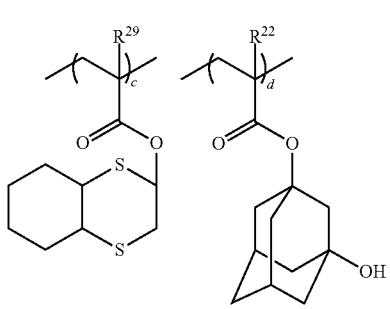
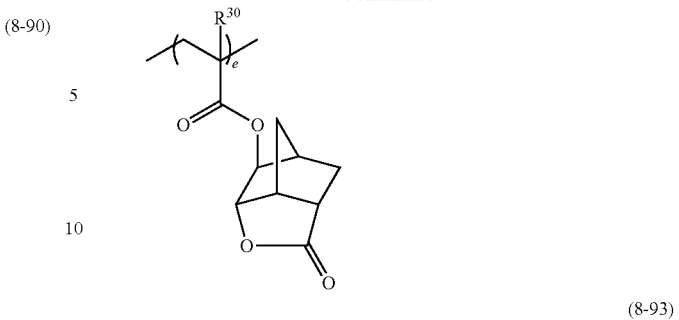
(8-93)
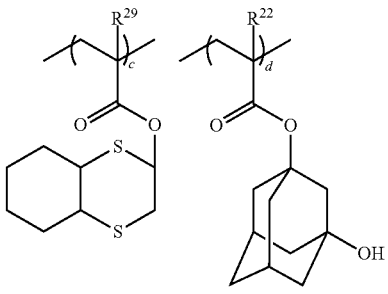
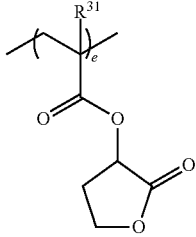
(8-94)
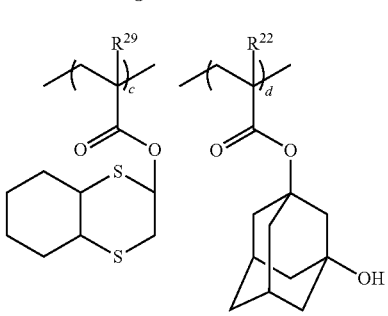
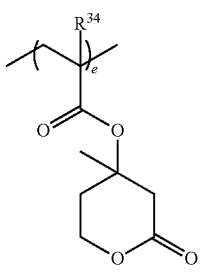
(8-95)
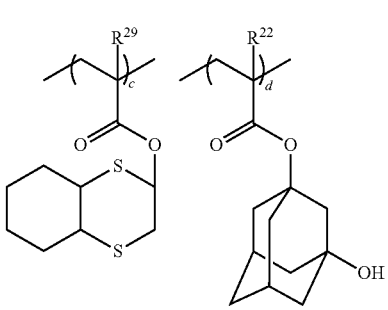

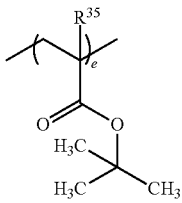

(8-96)

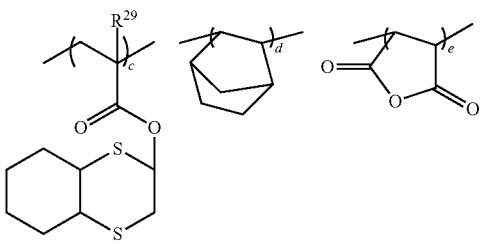

A weight average molecular weight (Mw) of the polymer (8) shall not specifically be restricted, and if it falls in a range of preferably 500 to 50,000, more preferably 1,000 to 30,000, a usefulness of the component of the photoresist composition described later is high. The above weight average molecular weight (Mw) is measured in the manner described in the example.

Photoresist Composition (9):

A photoresist composition can be prepared by blending the polymer (8) and a solvent, a photoacid generator and, if necessary, a basic compound, a surfactant and other additives each described later.

The photoresist composition (hereinafter referred to as the photoresist composition (9)) blended with the polymer (8) shall be explained below.

Solvent:

The solvent blended with the photoresist composition (9) includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like. They may be used alone or in a mixture of two or more kinds thereof.

A blending amount of the solvent falls in a range of usually 1 to 50 parts by mass, preferably 2 to 25 parts by mass based on 1 part by mass of the polymer (8).

Photoacid Generator:

The photoacid generator shall not specifically be restricted, and photoacid generators which have so far usually been used for chemically amplified resists can be used. The above photoacid generator includes, for example, nitrobenzyl derivatives such as 2-nitrobenzyl p-toluenesulfonate, 2,6-dinitrobenzyl p-toluenesulfonate, 2,4-dinitrobenzyl p-toluenesulfonate and the like; sulfonic esters such as 1,2,3-tris(methanesulfonyloxy)benzene, 1,2,3-tris(trifluoromethanesulfonyloxy)benzene, 1,2,3-tris(p-toluenesulfonyloxy)benzene and the like; diazomethane derivatives such as bis(benzenesulfonyl)diazomethane, bis(p-toluenesulfonyl)diazomethane, bis(2,4-dimethylphenylsulfonyl)diazomethane, bis(1,1-dimethylethysulfonyl)diazomethane, bis(cyclohexysulfonyl)diazomethane, bis(n-butylsulfonyl)diazomethane and the like; onium salts such as triphenylsulfonium trifluoromethanesulfonate, triphenylsulfonium nonafluoro-n-butanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, 1,2'-naphthylcarbonylmethyltetrahydrothiophenium triflate and the like; glyoxime derivatives such as bis-O-(p-toluenesulfonyl)-α-dimethyl glyoxime, bis-O-(n-butanesulfonyl)-α-dimethyl glyoxime and the like; sulfonic ester derivatives of N-hydroxyimide compounds such as N-hydroxysuccinimidemethanesulfonic esters, N-hydroxysuccinimidetrifluoromethanesulfonic esters, N-hydroxysuccinimide-1-propanesulfonic esters, N-hydroxyimide-p-toluenesulfonic esters, N-hydroxynaphthalimidemethanesulfonic esters, N-hydroxynaphthalimidebenzenesulfonic esters and the like; and halogen-containing triazine compounds such as 2-(4-methoxyphenyl)-4,6-bis(trichloromethyl)-1,3,5-triazine, 2-(4-methoxynaphthyl)-4,6-bis(trichloromethyl)-1,3,5-triazine, 2-(2-(2-furyl)ethenyl)-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine and the like. They may be used alone or in a mixture of two or more kinds thereof.

A blending amount of the photoacid generator falls usually in a range of preferably 0.1 to 30 parts by mass, more preferably 0.5 to 10 parts by mass based on 100 parts by mass of the polymer (8) described above from the viewpoint of securing a sensitivity and a development of the photoresist composition (9).

Basic Compound:

The photoresist composition (9) can be blended, if necessary, with a basic compound in an amount of a range in which the characteristics of the photoresist composition (9) are not inhibited in order to inhibit a diffusion rate of acid in the photoresist film to enhance a resolution thereof. The above basic compound includes, for example, amides such as formamide, N-methylformamide, N,N-dimethylformamide, acetamide, N-methylacetamide, N,N-dimethylacetamide, N-(1-adamantyl)acetamide, benzamide, N-acetylethanolamine, acetyl-3-methylpiperidine, pyrrolidone, N-methylpyrrolidone, ε-caprolactam, δ-valerolactam, 2-pyrrolidinone, acrylamide, methacrylamide, t-butylacrylamide, methylenebisacrylamide, methylenebismethacrylamide, N-methylolacrylamide, N-methoxyacrylamide, diacetoneacrylamide and the like; and amines such as pyridine, 2-methylpyridine, 4-methylpyridine, nicotine, quinoline, acridine, imidazole, 4-methylimidazole, benzimidazole, pyrazine, pyrazole, pyrrolidine, N-t-butoxycarbonylpyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine and the like. They may be used alone or in a mixture of two or more kinds thereof.

When the basic compound is blended, a blending amount thereof is varied depending on the kind of the basic compound used and falls usually in a range of preferably 0.01 to 10 mole, more preferably 0.05 to 1 mole based on 1 mole of the photoacid generator.

Surfactant:

The photoresist composition (9) can be further blended, if desired, with a surfactant in an amount of a range in which the characteristics of the photoresist composition (9) are not inhibited in order to enhance the coating property.

The above surfactant includes, for example, polyoxyethylene lauryl ether, polyoxyethylene stearyl ether, polyoxyethylene oleyl ether, polyoxyethylene n-octylphenyl ether and the like. They may be used alone or in a mixture of two or more kinds thereof.

When the surfactant is blended, a blending amount thereof is usually 2 parts by mass or less based on 100 parts by mass of the polymer (8).

Other Additives:

Further, the photoresist composition (9) can be blended with a sensitizer, a halation inhibitor, a form-improving agent, a storage stabilizer, a defoaming agent and the like as other additives in an amount of a range in which the characteristics of the photoresist composition (9) are not inhibited.

Formation of Photoresist Pattern:

The photoresist composition (9) is coated on a substrate and pre-baked usually at 70 to 160° C. for 1 to 10 minutes, and it is irradiated (exposed) with a radiation via a prescribed mask and then subjected to post exposure baking at 70 to 160° C. for 1 to 5 minutes to form a latent image pattern. Then, it is developed in a developer, whereby a prescribed resist pattern can be formed.

Radiations having various wavelengths, for example, a UV ray, an X ray and the like can be used for the exposure, and usually a g beam, an i beam and excimer lasers of XeCl, KrF, KrCl, ArF, ArCl and the like are used for a semiconductor resist. Among them, an ArF excimer laser is preferably used from the viewpoint of fine processing.

An exposure dose thereof falls in a range of preferably 0.1 to 1,000 mJ/cm$^2$, more preferably 1 to 500 mJ/cm$^2$.

The developer includes, for example, inorganic bases such as sodium hydroxide, potassium hydroxide, sodium carbonate, aqueous ammonia and the like; alkylamines such as ethylamine, diethylamine, triethylamine and the like; alcoholamines such as dimethylethanolamine, triethanolamine and the like; and alkaline aqueous solutions prepared by dissolving quaternary ammonium salts such as tetramethylammonium hydroxide, tetraethylammonium hydroxide and the like. Among them, preferably used are the alkaline aqueous solutions prepared by dissolving quaternary ammonium salts such as tetramethylammonium hydroxide, tetraethylammonium hydroxide and the like.

A concentration of the developer falls usually in a range of preferably 0.1 to 20% by mass, more preferably 0.1 to 10% by mass.

Liquid Immersion Lithography:

The photoresist composition (9) can be applied to a liquid immersion lithography. When the photoresist composition (9) is applied to the liquid immersion lithography, purified water or a liquid for liquid immersion lithography in which a refractive index in a wavelength of 193 nm is not smaller than a refractive index of water can be used as an immersion liquid.

The immersion liquid in which a refractive index in a wavelength of 193 nm is not smaller than a refractive index of water shall not specifically be restricted as long as the refractive index in a wavelength of 193 nm is not smaller than a refractive index (1.44) of water, and various liquids can be used.

When a photoresist film is formed by the photoresist composition (9), the photoresist film having a refractive index of 1.72 or more in a wavelength of 193 nm can be obtained. Even when an immersion liquid (an immersion liquid having a high refractive index) having a refractive index of 1.70 or more in a wavelength of 193 nm is used in a liquid immersion lithographic step, the problem that exposure light is reflected wholly on an interface between the immersion liquid and the photoresist film is less liable to be brought about, and the basic performances can be prevented from deterioration (for example, a reduction in the sensitivity) which originates in whole reflection of exposure light.

A refractive index of the photoresist film described above is a value measured by irradiating the photoresist film having a thickness of 30 to 300 nm with light having a wavelength of 193 nm by means of a spectroscopic ellipsometer (for example, VUV-VASE, manufactured by J. A. Woollam Co., Inc.).

EXAMPLES

The present invention shall be explained in further details with reference to examples, but the present invention shall by no means be restricted by these examples. The measuring methods of Mw and Mn in the respective examples and a calculating method of the dispersion degree are shown below.

Measurement of Mw and Mn and Calculation of Dispersion Degree:

The weight average molecular weight (Mw) and the number average molecular weight (Mn) were measured on the following conditions by gel permeation chromatography (GPC) using tetrahydrofuran (THF) as an eluant by means of a differential refractometer used as a detector, and they were determined as values converted by a calibration curve prepared using standard polystyrene. Further, the dispersion degree (Mw/Mn) was determined by dividing the weight average molecular weight (Mw) by the number average molecular weight (Mn).

GPC Measurement:

Used was a column obtained by connecting serially two columns of TSK-gel SUPER HZM-H (trade name, 4.6 mm×150 mm, manufactured by Tosoh Corp.) and one column of TSK-gel SUPER HZ2000 (trade name, 4.6 mm×150 mm, manufactured by Tosoh Corp.), and measurement was carried out on the conditions of a column temperature of 40° C., a differential refractometer temperature of 40° C. and a flow velocity of 0.35 mL/minute in the eluant.

Synthetic Example 1

Synthesis of 2-chloro-1-methoxyethyl=acetate (First Step)

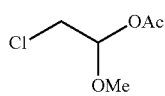

A four neck flask having a content volume of 500 mL equipped with a thermometer, a dropping funnel and a stirring device was charged with 169.3 g (1.36 mol) of chloroacetaldehyde=dimethyl=acetal and 139.3 g (1.37 mol) of acetic anhydride. The flask was cooled on a water bath, and 0.27 g of conc. sulfuric acid was slowly dropwise added thereto while stirring. The mixture was stirred at an inside temperature falling in a range of 20 to 30° C. for 50 hours and then stirred at 50° C. for 3 hours while heating. An inside temperature of the reaction solution was lowered down to room temperature, and then it was transferred into a separating funnel of 1 L. Diisopropyl ether 147.8 g was put thereinto to wash the solution twice with 59.0 g of a 7% sodium hydrogencarbonate aqueous solution, and the solvent was removed by distillation under reduced pressure to obtain 221.8 g of a crude for distillation. A molecular distillation equipment "MS-300" (manufactured by SHIBATA SCIENTIFIC TECHNOLOGY LTD.) was used for the distillation. The above crude was allowed to flow therethrough at a pressure of 1,330 Pa and a temperature of 30° C. to obtain 188.5 g of a high boiling fraction. The above high boiling fraction was allowed to flow therethrough at a pressure of 1,330 Pa and a temperature of 40 to 50° C. to obtain 163.5 g (1.01 mol) of 2-chloro-1-methoxyethyl=acetate as a low boiling fraction in the form of a colorless and transparent oil (purity: 94.0%, yield: 74%).

Reference Example 1

Case in which Lithium Hydride was Used as a Base in Synthesis of 1,4-dithiane-2-ol (Second Step)

A three neck flask having a content volume of 50 mL equipped with a thermometer, a dropping funnel and a stirring device was charged with 10.4 g of 1,2-dimethoxyethane, and an inside of the flask was substituted with nitrogen. The flask was charged with 108 mg (12.9 mmol) of lithium hydride while cooling it on a water bath, and the mixture was for 15 minutes. 1,2-Ethanedithiol 1.13 g (12.0 mmol) was slowly dropwise added thereto so that the temperature was maintained in a range of 25 to 30° C. In this case, gas was observed to be generated. After stirring for about 30 minutes since finishing dropwise adding, 974 mg (6.00 mmol) of 2-chloro-1-methoxyethyl=acetate obtained in Synthetic Example 1 was slowly dropwise added thereto from the dropping funnel so that the temperature was maintained in a range of 25 to 30° C. After finishing dropwise adding, stirring was continued at 25 to 35° C. for one hour, and the reaction solution was analyzed by gas chromatography. The results thereof are shown in Table 1.

Example 1

Case in which Sodium Hydride was Used as a Base in Synthesis of 1,4-dithiane-2-ol (Second Step)

The experiment was carried out in the same manner as in Reference Example 1, except that in Reference Example 1, 516 mg (12.9 mmol) of sodium hydride (60%) was used in place of 108 mg (12.9 mmol) of lithium hydride. The results thereof are shown in Table 1.

Hydrolysis of 1,4-dithiane-2-yl=acetate

Water 6.8 g was slowly dropwise added to the reaction solution obtained at a temperature falling in a range of 25 to 40° C. while cooling the flask on a water bath. Immediately after finishing dropwise adding, the pH was confirmed with a pH test paper to find that it was 12. After finishing dropwise adding, stirring was continued while maintaining the inside temperature at 60° C. A change in 1,4-dithiane-2-ol and 1,4-dithiane-2-yl=acetate was traced by gas chromatography. The results thereof are shown in Table 2.

TABLE 1 comparison of reaction results according to the kind of the base in synthesis of 1,4-dithiane-2-ol

| Base | Conversion rate of 2-chloro-1-methoxyethyl = acetate*[1] (%) | Selectivity (%) | |
|---|---|---|---|
| | | 1,4-dithiane-2-ol*[2] | 1,4-dithiane-2-yl = acetate*[3] |
| Lithium hydride | About 100 | 73.4 | 8.2 |
| Sodium hydride | About 100 | 32.1 | 65.3 |

*[1] calculated according to (total of area of the whole peaks in the compounds produced in the reaction) ÷ [(area of a peak of 2-chloro-1-methoxyethyl = acetate) + (total of area of the whole peaks in the compounds produced in the reaction)] × 100
*[2] calculated according to (area of a peak of 1,4-dithiane-2-ol) ÷ (total of area of the whole peaks in the compounds produced in the reaction) × 100
*[3] calculated according to (area of a peak of 1,4-dithiane-2-yl = acetate) ÷ (total of area of the whole peaks in the compounds produced in the reaction) × 100

TABLE 2 results of hydrolysis test of 1,4-dithiane-2-yl = acetate

| Time (hr) | Selectivity (%) | | Yield of 1,4-dithiane-2-ol*[3] (%) |
|---|---|---|---|
| | 1,4-dithiane-2-ol-*[1] | 1,4-dithiane-2-yl = acetate*[2] | |
| 0 | 32.1 | 65.3 | 37.5 |
| 5 | 66.5 | 20.6 | 69.3 |
| 8 | 72.4 | 13.9 | 78.0 |
| 11 | 74.3 | 9.8 | 77.9 |

*[1] calculated according to (area of a peak of 1,4-dithiane-2-ol) ÷ (total of area of the whole peaks in the compounds produced in the reaction) × 100
*[2] calculated according to (area of a peak of 1,4-dithiane-2-yl = acetate) ÷ (total of area of the whole peaks in the compounds produced in the reaction) × 100
*[3] calculated according to an internal standard determination method using n-decane for an internal standard It has been found from the results shown in Table 1 that when sodium hydride is used, a proceeding degree of the reaction is the same as in a case of lithium hydride but a selectivity of targeted 1,4-dithiane-2-ol is low and that a cause therefor resides in a large production amount of 1,4-dithiane-2-yl=acetate.

Further, it has been found from the results shown in Table 2 that when sodium hydride is used as the base, 1,4-dithiane-2-yl=acetate which is by-produced in a large amount can efficiently be converted into targeted 1,4-dithiane-2-ol only by heating and stirring on an alkaline condition in which water is added to the reaction solution. According to the above method, a method using lithium hydride which is difficult to be industrially carried out can be avoided.

Example 2

Production of 1,4-dithiane-2-ol (Second Step)

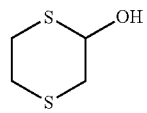

A four neck flask having a content volume of 3 L equipped with a thermometer, a dropping funnel and a stirring device was charged with 1,390 g of 1,2-dimethoxyethane, and an inside of the flask was substituted with nitrogen. The flask was charged with 79.0 g (1.96 mol) of sodium hydride (60%) while cooling it on a water bath, and the mixture was stirred for 30 minutes. The flask was equipped with a reflux condensor, and then 181.2 g (1.92 mol) of 1,2-ethanedithiol was slowly dropwise added thereto from the dropping funnel so that the temperature was maintained in a range of 25 to 30° C. In this case, gas was observed to be generated. After stirring for 30 minutes since finishing dropwise adding, 154.3 g (0.96 mol) of 2-chloro-1-methoxyethyl=acetate obtained in Synthetic Example 1 was slowly dropwise added thereto from the dropping funnel so that the temperature was maintained in a range of 25 to 30° C. After finishing dropwise adding, stirring was continued at 25 to 35° C. for 3 hours. In this regard, the reaction solution was analyzed by gas chromatography to find that a conversion rate of 2-chloro-1-methoxyethyl=acetate was 99.2%.

Hydrolysis of 1,4-dithiane-2-yl=acetate

Water 906.5 g was slowly dropwise added from the dropping funnel at a temperature falling in a range of 25 to 60° C., and after finishing dropwise adding, stirring was continued for 12 hours while maintaining the temperature at 60° C. by heating the water bath. In this regard, the reaction solution was analyzed by gas chromatography to find that a ratio of 1,4-dithiane-2-ol to 1,4-dithiane-2-yl=acetate was 1,4-dithiane-2-ol:1,4-dithiane-2-yl=acetate=85:15 (area ratio).

A 10% hydrochloric acid aqueous solution was dropwise added from the dropping funnel at a temperature falling in a of 10 to 15° C. to adjust the pH to 8.1 (added amount: 112.6 g). The solution obtained was transferred into a separating funnel having a content volume of 5 L and extracted twice with 1670 g of diisopropyl ether. The extract of two extractions thus obtained was put into a separating funnel having a content volume of 5 L and washed in order with 801 g of water and 504 g of a saturated brine, and the solvent was removed by distillation under reduced pressure to obtain 285.9 g of a concentrate. Diisopropyl ether 47.5 g, n-hexane 85.2 g and a small amount of a crystal seed were added to the concentrate thus obtained, and the mixture was slowly cooled down to 0° C. The deposit was separated by filtering and transferred into a flask of 300 mL, and 320 g of n-hexane was added thereto. The mixture was stirred at 25° C. for 1 hour. The deposit was separated again by filtering and dried at room temperature under reduced pressure to obtain 73.8 g (0.52 mol) of 1,4-dithiane-2-ol showing the following physical properties in the form of a white solid (purity: 94.1%, yield: 53%).

$^1$H-NMR (300 MHz, CDCl$_3$, TMS, ppm) δ: 2.52 to 2.62 (3H, m), 2.85 (1H, dd, J=2.1, 13.4 Hz), 3.52 to 3.64 (1H, br), 3.86 (1H, ddd, J=5.0, 5.2, 12.1 Hz), 4.28 (1H, ddd, J=4.8, 4.9, 12.1 Hz), 5.03 (1H, ddd, J=1.9, 5.8, 7.7 Hz).

Example 3

Production of 1,4-dithiane-2-yl=methacrylate (Third Step)

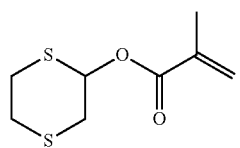

A four neck flask having a content volume of 1 L equipped with a thermometer, a dropping funnel and a stirring device was charged with 34.5 g (238 mmol) of 1,4-dithiane-2-ol obtained in Example 2, 349.3 g of THF and 0.47 g of phenothiazine, and an inside of the flask was substituted with nitrogen. Triethylamine 48.2 g (476 mmol) was dropwise added thereto from the dropping funnel so that the temperature was maintained in a range of 5 to 8° C. in a state in which the flask was cooled on an ice bath.

Next, 30.4 g (287.9 mmol) of methacrylic chloride was dropwise added thereto so that the temperature was maintained in a range of 5 to 10° C. After finishing dropwise adding, stirring was continued at 3 to 6° C. for 2.5 hours. In this regard, the reaction solution was analyzed by gas chromatography to find that a conversion rate of 1,4-dithiane-2-ol was 99.6%.

Water 233 g was slowly dropwise added from the dropping funnel so that the temperature was maintained at lower than 20° C., and after finishing dropwise adding, the ice bath was removed to leave the inside temperature to 24° C. 4-Dimethylaminopyridine 1.46 g was added thereto, and the mixture was stirred at 24 to 26° C. for 2 hours. In this regard, the reaction solution was analyzed by gas chromatography to find that a ratio of methacrylic anhydride to 1,4-dithiane-2-yl=methacrylate was methacrylic anhydride:1,4-dithiane-2-yl=methacrylate=0.1:99.9 (area ratio).

The solution obtained was transferred into a separating funnel having a content volume of 2 L and extracted three times with 240 g of ethyl acetate. The extract of three extractions thus obtained was put into a separating funnel having a content volume of 2 L and washed in order with three times 230 g of a 1% hydrochloric acid aqueous solution, 116 g of water, 118 g of a saturated sodium hydrogencarbonate aqueous solution, twice 118 g of water and 100 g of a saturated brine. p-Methoxyphenol 0.010 g and phenothiazine 0.020 g were added thereto, and the solvent was removed by distillation under reduced pressure to obtain 55.0 g of a crude for distillation. A molecular distillation equipment "MS-300" (manufactured by SHIBATA SCIENTIFIC TECHNOLOGY LTD.) was used for the distillation. The above crude was allowed to flow therethrough at a pressure of 13.3 to 20.0 Pa and a temperature of 40 to 45° C. to obtain 47.4 g of a high boiling fraction. The above high boiling fraction was allowed to flow therethrough at a pressure of 10.7 to 13.3 Pa and a temperature of 55 to 60° C. to obtain 37.8 g (182 mmol) of 1,4-dithiane-2-yl=methacrylate showing the following physical properties as a low boiling fraction in the form of a colorless and transparent oil (purity: 98.4%, yield: 76%).

Also, log P which is a log value of an octanol/water distribution coefficient and SP which is a solubility parameter were calculated by using Hamiltonian PM5 of a calculation soft "CAChe" (trade name, manufactured by Fujitsu Limited).

$^1$H-NMR (300 MHz, CDCl$_3$, TMS, ppm) δ: 2.00 (3H, s), 2.68 to 2.82 (2H, m), 2.94 (1H, dd, J=5.2, 14.1 Hz), 3.10 (1H, ddd, J=2.2, 13.2 Hz), 3.30 to 3.41 (2H, m), 5.67 (1H, s), 5.87 to 5.92 (1H, m), 6.28 (1H, s)

log P: 1.77
SP: 17.6 (J/mol)$^{0.5}$

Example 4

Production of 1,4-dithiepane-2-ol (Second Step)

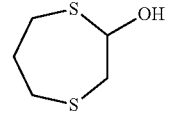

A four neck flask of 3 L equipped with a thermometer, a dropping funnel and a stirring device was charged with 1390 g of 1,2-dimethoxyethane, and an inside of the flask was substituted with nitrogen. The flask was charged with 79.0 g (1.96 mol) of sodium hydride (60%) while cooling it on a water bath, and the mixture was stirred for 30 minutes. The flask was equipped with a reflux condensor, and then 209.9 g (1.92 mol) of 1,3-propanedithiol was slowly dropwise added thereto from the dropping funnel so that the temperature was maintained in a range of 25 to 30° C. In this case, gas was observed to be generated. After stirring for 30 minutes since finishing dropwise adding, 154.3 g (0.96 mol) of 2-chloro-1-methoxyethyl=acetate obtained in Synthetic Example 1 was slowly dropwise added thereto from the dropping funnel so that the temperature was maintained in a range of 25 to 30° C. After finishing dropwise adding, stirring was continued at 25 to 35° C. for 5 hours. In this regard, the reaction solution was analyzed by gas chromatography to find that a conversion rate of 2-chloro-1-methoxyethyl=acetate was 98.9%.

Hydrolysis of 1,4-dithiepane-2-yl=acetate

Water 906.0 g was slowly dropwise added from the dropping funnel at a temperature falling in a range of 25 to 60° C., and after finishing dropwise adding, stirring was continued for 12 hours while maintaining the temperature at 60° C. by heating the water bath. In this regard, the reaction solution was analyzed by gas chromatography to find that a ratio of 1,4-dithiepane-2-ol to 1,4-dithiepane-2-yl=acetate was 1,4-dithiepane-2-ol 1,4-dithiepane-2-yl=acetate=82:18 (area ratio).

A 10% hydrochloric acid aqueous solution was dropwise added from the dropping funnel at a temperature falling in a range of 10 to 15° C. to adjust the pH to 6.2. The solution obtained was transferred into a separating funnel having a content volume of 5 L and extracted twice with 1650 g of diisopropyl ether. The extract of two extractions thus obtained was put into a separating funnel having a content volume of 5 L and washed in order with 800 g of water and 500 g of a saturated brine, and the solvent was removed by distillation under reduced pressure. The concentrate was refined by silica gel chromatography to thereby obtain 40.8 g (0.26 mol) of 1,4-dithiepane-2-ol (purity: 97.1%, yield: 27.5%).

Example 5

Production of 1,4-dithiepane-2-yl=methacrylate
(Third Step)

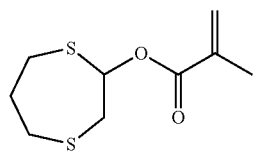

A four neck flask having a content volume of 100 ml equipped with a thermometer, a dropping funnel and a stirring device was charged with 3.68 g (23.8 mmol) of 1,4-dithiepane-2-ol obtained in Example 4, 34.9 g of THF and 47 mg of phenothiazine, and an inside of the flask was substituted with nitrogen. Triethylamine 4.82 g (47.6 mmol) was dropwise added thereto from the dropping funnel so that the temperature was maintained in a range of 5 to 8° C. in a state in which the flask was cooled on an ice bath.

Next, 3.04 g (28.8 mmol) of methacrylic chloride was dropwise added thereto so that the temperature was maintained in a range of 5 to 10° C. After finishing dropwise adding, stirring was continued at 3 to 7° C. for 3 hours. In this regard, the reaction solution was analyzed by gas chromatography to find that a conversion rate of 1,4-dithiepane-2-ol was 99.2%.

Water 23.3 g was slowly dropwise added from the dropping funnel so that the temperature was maintained at lower than 20° C., and after finishing dropwise adding, the ice bath was removed to leave the inside temperature to 24° C. 4-Dimethylaminopyridine 0.15 g was added thereto, and the mixture was stirred at 23 to 26° C. for 2 hours. In this regard, the reaction solution was analyzed by gas chromatography to find that a ratio of methacrylic anhydride to 1,4-dithiepane-2-yl=methacrylate was methacrylic anhydride: 1,4-dithiepane-2-yl=methacrylate=0.1:99.9 (area ratio). The solution obtained was transferred into a separating funnel having a content volume of 200 mL and extracted three times with 25 g of ethyl acetate. The extract of three extractions thus obtained was put into a separating funnel having a content volume of 200 mL and washed in order with three times 23 g of a 1% hydrochloric acid aqueous solution, 15 g of water, 15 g of a saturated sodium hydrogencarbonate aqueous solution, twice 15 g of water and 10 g of a saturated brine. p-Methoxyphenol 2.0 mg and phenothiazine 2.0 mg were added thereto, and the solvent was removed by distillation under reduced pressure. The concentrate was refined by silica gel chromatography to thereby obtain 4.36 g (19.5 mmol) of 1,4-dithiepane-2-yl=methacrylate (purity: 97.7%, yield: 81.9%).

Example 6

Production of 5,6-dimethyl-1,4-dithiane-2-ol
(Second Step)

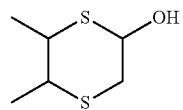

A four neck flask of 300 mL equipped with a thermometer, a dropping funnel and a stirring device was charged with 139 g of 1,2-dimethoxyethane, and an inside of the flask was substituted with nitrogen. The flask was charged with 7.90 g (197 mmol) of sodium hydride (60%) while cooling it on a water bath, and the mixture was stirred for 30 minutes. The flask was equipped with a reflux condensor, and then 24.2 g (192 mmol) of 2,3-butanedithiol was slowly dropwise added thereto from the dropping funnel so that the temperature was maintained in a range of 25 to 30° C. In this case, gas was observed to be generated. After stirring for 30 minutes since finishing dropwise adding, 15.4 g (94.9 mmol) of 2-chloro-1-methoxyethyl=acetate obtained in Synthetic Example 1 was slowly dropwise added thereto from the dropping funnel so that the temperature was maintained in a range of 25 to 30° C. After finishing dropwise adding, stirring was continued at 25 to 30° C. for 5 hours. In this regard, the reaction solution was analyzed by gas chromatography to find that a conversion rate of 2-chloro-1-methoxyethyl=acetate was 98.8%.

Hydrolysis of 5,6-dimethyl-1,4-dithiane-2-yl=acetate

Water 90.0 g was slowly dropwise added from the dropping funnel at a temperature falling in a range of 25 to 60° C., and after finishing dropwise adding, stirring was continued for 12 hours while maintaining the temperature at 60° C. by heating the water bath. In this regard, the reaction solution was analyzed by gas chromatography to find that a ratio of 5,6-dimethyl-1,4-dithiane-2-ol to 5,6-dimethyl-1,4-dithiane-2-yl=acetate was 5,6-dimethyl-1,4-dithiane-2-ol: 5,6-dimethyl-1,4-dithiane-2-yl=acetate=88:12 (area ratio).

A 10% hydrochloric acid aqueous solution was dropwise added from the dropping funnel at a temperature falling in a range of 10 to 15° C. to adjust the pH to 8.2. The solution obtained was transferred into a separating funnel having a content volume of 500 ml, and extracted twice with 160 g of diisopropyl ether. The extract of two extractions thus obtained was put into a separating funnel having a content volume of 500 mL and washed in order with 10 g of water and 20 g of a saturated brine, and the solvent was removed by distillation under reduced pressure. The concentrate was refined by silica gel chromatography to thereby obtain 9.09 g (54.1 mmol) of 5,6-dimethyl-1,4-dithiane-2-ol (purity: 97.8%, yield: 57.0%).

Example 7

Production of 5,6-dimethyl-1,4-dithiane-2-yl=methacrylate (Third Step)

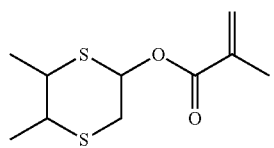

A four neck flask having a content volume of 100 mL equipped with a thermometer, a dropping funnel and a stirring device was charged with 4.00 g (23.8 mmol) of 5,6-dimethyl-1,4-dithiane-2-ol obtained in Example 6, 34.9 g of THF and 47 mg of phenothiazine, and an inside of the flask was substituted with nitrogen. Triethylamine 4.82 g (47.6 mmol) was dropwise added thereto from the dropping funnel so that the temperature was maintained in a range of 5 to 8° C. in a state in which the flask was cooled on an ice bath.

Next, 3.04 g (28.8 mmol) of methacrylic chloride was dropwise added thereto so that the temperature was maintained in a range of 5 to 10° C. After finishing dropwise adding, stirring was continued at 3 to 7° C. for 3 hours. In this regard, the reaction solution was analyzed by gas chromatography to find that a conversion rate of 5,6-dimethyl-1,4-dithiane-2-ol was 99.0%.

Water 23.3 g was slowly dropwise added from the dropping funnel so that the temperature was maintained at lower than 20° C., and after finishing dropwise adding, the ice bath was removed to leave the inside temperature to 24° C. 4-Dimethylaminopyridine 0.15 g was added thereto, and the mixture was stirred at 23 to 26° C. for 2 hours. In this regard, the reaction solution was analyzed by gas chromatography to find that a ratio of methacrylic anhydride to 5,6-dimethyl-1,4-dithiane-2-yl=methacrylate was methacrylic anhydride: 5,6-dimethyl-1,4-dithiane-2-yl=methacrylate=0.1:99.9 (area ratio).

The solution obtained was transferred into a separating funnel having a content volume of 200 mL and extracted three times with 25 g of ethyl acetate. The extract of three extractions thus obtained was put into a separating funnel having a content volume of 200 mL and washed in order with three times 23 g of a 1% hydrochloric acid aqueous solution, 15 g of water, 15 g of a saturated sodium hydrogencarbonate aqueous solution, twice 15 g of water and 10 g of a saturated brine. p-Methoxyphenol 2.0 mg and phenothiazine 2.0 mg were added thereto, and the solvent was removed by distillation under reduced pressure. The concentrate was refined by silica gel chromatography to thereby obtain 4.85 g (20.3 mmol) of 5,6-dimethyl-1,4-dithiane-2-yl=methacrylate (purity: 97.2%, yield: 85.3%).

Example 8

Evaluation of a Reactivity of the Acrylic Ester Derivative (1) to Acid

An NMR tube was charged with $2.73 \times 10^{-4}$ mol of 1,4-dithiane-2-yl=methacrylate obtained in Example 3, 0.69 mL of 1,1,2,2-tetrachloroethane-$d_2$ and $1.47 \times 10^{-6}$ mol of methanesulfonic acid, and it was provided with a cap and shaken up well.

The above NMR tube was dipped in an oil bath of 120° C. for several seconds to several minutes, and then the NMR tube was taken out and put in an ice bath to cool the reaction solution. Then, $^1$H-NMR thereof was immediately measured by means of "NMR Gemini-300" (trade name, manufactured by Varian Technologies Limited). Unreacted methacrylic ester and acrylic acid produced by the reaction were observed in the NMR chart of methacrylic ester reacted, and a conversion rate in the dissociation reaction was determined from the respective vinyl protons. Thereafter, an operation in which the above NMR tube was dipped in the oil bath of 120° C. for several seconds to several minutes and cooled in the ice bath to measure the $^1$H-NMR was repeated several times to determine the conversion rates to the reaction time in several points. The conversion rates versus the reaction time determined above were plotted on an X axis of the time (s) and a Y axis of ln(1–X) according to the following primary reaction rate equation $$-kt = \ln(1-X) \quad \text{(Equation 1)}$$

(wherein k represents a rate constant (s$^{-1}$); t represents time (s); and X represents a conversion rate), and a rate constant in deprotection reaction of methacrylic ester at 120° C. was determined from a gradient of the straight line.

2-Methacryloyloxy-2-methyladamantane which was usually used was selected as a comparative object to determine the rate constant at 120° C. by the same method as in 1,4-dithiane-2-yl=methacrylate. A relative activity of 1,4-dithiane-2-yl=methacrylate to 2-methacryloyloxy-methyladamantane was determined by dividing a rate constant in deprotection reaction of 1,4-dithiane-2-yl=methacrylate by a rate constant in deprotection reaction of 2-methacryloyloxy-2-methyladamantane, and it was set to an index of the reactivity (activity in deprotection reaction) to acid.

The operation and the analysis described above were carried out at 140° C. The results thereof are shown in Table 3.

Example 9

Evaluation of a Reactivity of the Acrylic Ester Derivative (1) to Acid

The experiment was carried out in the same manner as in Example 8, except that in Example 8, 1,4-dithiepane-2-yl=methacrylate obtained in Example 5 was used in place of 1,4-dithiane-2-yl=methacrylate, and the reactivity (activity in deprotection reaction) to acid was evaluated by the same method. The results thereof are shown in Table 3.

Example 10

Evaluation of a Reactivity of the Acrylic Ester Derivative (1) to Acid

The experiment was carried out in the same manner as in Example 8, except that in Example 8, 5,6-dimethyl-1,4-dithiane-2-yl=methacrylate obtained in Example 7 was used in place of 1,4-dithiane-2-yl=methacrylate, and the reactivity (activity in deprotection reaction) to avid was evaluated by the same method. The results thereof are shown in Table 3.

TABLE 3 relative activity in deprotection reaction in the presence of methanesulfonic acid

| Acrylic ester derivative (1) | 2-methacryloyloxy-2-methyladamantane | Example 8 1,4-dithiane-2-yl = methacrylate | Example 9 1,4-dithiepane-2-y1 = methacrylate | Example 10 5,6-dimethyl-1,4-dithiane-2-yl = methacrylate |
|---|---|---|---|---|
| Relative activity (120° C.) | 1.00 | 6.95 | 4.23 | 6.02 |
| Relative activity (140° C.) | 1.00 | 4.12 | 3.22 | 3.99 |

Examples 11 to 13

Activation Energy in Deprotection Reaction of the Acrylic Ester Derivative (1)

The rate constants in the deprotection reaction at 120° C. and 140° C. which were determined by analysis in Examples 8 to 10 were substituted for the following equation (Equation 2) to determine the activation energy (E) in the deprotection reaction of the respective acrylic ester derivatives (1). The results thereof are shown in Table 4.

$$\log \frac{k_2}{k_1} = \frac{E}{2.303R}\left(\frac{1}{T_1} - \frac{1}{T_2}\right) \quad \text{(Equation 2)}$$

(wherein $k_1$ represents a rate constant ($s^{-1}$) in the deprotection reaction at 120° C.; $k_2$ represents a rate constant ($s^{-1}$) in the deprotection reaction at 140° C.; E represents an activation energy (kcal/mol) in the deprotection reaction; R represents an air constant (1.987 cal·$K^{-1}$·$mol^{-1}$; $T_1$ represents an absolute temperature (K) of 120° C.; $T_2$ represents an absolute temperature (K) of 140° C.).

TABLE 4 activation energy in deprotection reaction

| Acrylic ester derivative (1) | 2-methacryloyloxy-2-methyladamantane | Example 11 1,4-dithiane-2-yl = methacrylate | Example 12 1,4-dithiepane-2-yl = methacrylate | Example 13 5,6-dimethyl-1,4-dithiane-2-yl = methacrylate |
|---|---|---|---|---|
| Activation energy (kcal/mol) | 18.8 | 10.3 | 14.4 | 12.1 |

It has been found from the results shown in Tables 3 and 4 that when compared with publicly known methacrylic esters, the acrylic ester derivatives (1) of the present invention have a high reactivity to acids (refer to Examples 8 to 11) and that they have a low activation energy (refer to Examples 11 to 13), and therefore they are useful as raw materials for chemically amplified resists.

Synthetic Example 2

Synthesis of Polymer (a)

A round-bottom flask having a content volume of 50 mL equipped with an electromagnetic stirring device, a reflux condenser and a thermometer was charged with 1.00 g (4.89 mmol) of 1,4-dithiane-2-yl=methacrylate obtained in Example 3, 4.00 g of 1,4-dioxane and 99.7 mg (0.401 mmol) of 2,2'-azobis(2,4-dimethylvaleronitrile) under nitrogen atmosphere to carry out polymerization reaction at 60° C. for 3 hours.

A reaction mixture obtained was dropwise added to methanol of about 20 mass per mass of the reaction mixture at room temperature while stirring, and a precipitate produced was separated by filtering and washed with methanol of the same mass as described above, whereby a white precipitate was obtained. The above precipitate was dried at 50° C. for 10 hours under reduced pressure (26.7 Pa) to obtain 0.56 g of a polymer (a) comprising a repetitive unit shown below. The polymer (a) thus obtained had Mw of 23,800 and a dispersion degree of 2.90.

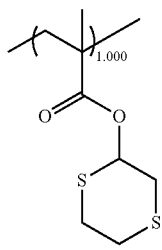

Synthetic Example 3

Synthesis of Polymer (b)

A round-bottom flask having a content volume of 200 mL equipped with an electromagnetic stirring device, a reflux condenser and a thermometer was charged with 8.16 g (39.1 mmol) of 1,4-dithiane-2-yl=methacrylate obtained in Example 3, 9.25 g (39.1 mmol) of 3-hydroxy-1-adamantyl=methacrylate, 168.0 g of 1,4-dioxane and 1.95 g (7.86 mmol) of 2,2'-azobis(2,4-dimethylvaleronitrile) under nitrogen atmosphere to carry out polymerization reaction at 60 to 65° C. for 4 hours.

A reaction mixture obtained was dropwise added to methanol of about 20 mass per mass of the reaction mixture at room temperature while stirring, and a precipitate produced was separated by filtering. The above precipitate was dissolved in 150.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 10.3 g of a polymer (b) comprising a repetitive unit shown below. The polymer (b) thus obtained had Mw of 13,600 and a dispersion degree of 1.50.

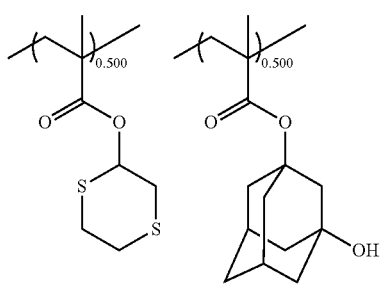

Synthetic Example 4

Synthesis of Polymer (c)

A round-bottom flask having a content volume of 200 mL equipped with an electromagnetic stirring device, a reflux condenser and a thermometer was charged with 8.00 g (38.4 mmol) of 1,4-dithiane-2-yl=methacrylate obtained in Example 3, 8.53 g (38.4 mmol) of 5-methacryloyloxy-2,6-norbornanecarbolactone, 130.0 g of 1,4-dioxane and 3.89 g (15.7 mmol) of 2,2'-azobis(2,4-dimethylvaleronitrile) under nitrogen atmosphere to carry out polymerization reaction at 60 to 65° C. for 3 hours.

A reaction mixture obtained was dropwise added to methanol of about 20 mass per mass of the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 12.1 g of a polymer (c) comprising a repetitive unit shown below. The polymer (c) thus obtained had Mw of 10,600 and a dispersion degree of 1.83.

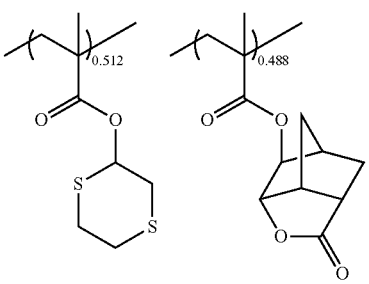

Synthetic Example 5

Synthesis of Polymer (d)

Polymerization reaction was carried out in the same charge amounts on the same conditions as in Synthetic Example 4, except that in Synthetic Example 4, 6.53 g (38.4 mmol) of α-methacryloyloxy-γ-butyrolactone was used in place of 8.53 g (38.4 mmol) of 5-methacryloyloxy-2,6-norbornanecarbolactone and that a use amount of 2,2'-azobis(2,4-dimethylvaleronitrile) was changed from 3.89 g (15.7 mmol) to 1.95 g (7.83 mmol).

A reaction mixture obtained was dropwise added to methanol of about 20 mass per mass of the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 9.4 g of a polymer (d) comprising a repetitive unit shown below. The polymer (d) thus obtained had Mw of 8,600 and a dispersion degree of 1.67.

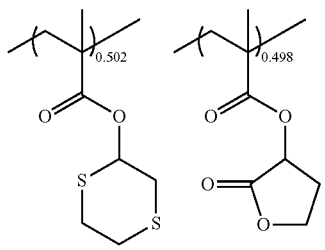

Synthetic Example 6

Synthesis of Polymer (e)

Polymerization reaction was carried out in the same charge amounts on the same conditions as in Synthetic Example 5, except that in Synthetic Example 5, a use amount of α-methacryloyloxy-γ-butyrolactone was changed from 6.53 g (38.4 mmol) to 4.36 g (25.6 mmol) and that a use amount of 2,2'-azobis(2,4-dimethylvaleronitrile) was changed from 1.95 g (7.83 mmol) to 1.64 g (6.62 mmol).

A reaction mixture obtained was dropwise added to methanol of about 20 mass per mass of the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 10.2 g of a polymer (e) comprising a repetitive unit shown below. The polymer (e) thus obtained had Mw of 9,900 and a dispersion degree of 1.75.

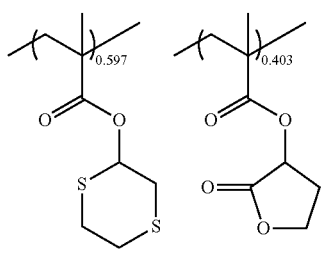

Synthetic Example 7

Synthesis of Polymer (f)

A round-bottom flask having a content volume of 100 mL equipped with an electromagnetic stirring device, a reflux condenser and a thermometer was charged with 3.88 g (18.7 mmol) of 1,4-dithiane-2-yl=methacrylate obtained in Example 3, 2.95 g (12.5 mmol) of 3-hydroxy-1-adamantyl=methacrylate, 4.16 g (18.7 mmol) of 5-methacryloyloxy-2,6-norbornanecarbolactone, 100.0 g of 1,4-dioxane and 2.48 g (10.0 mmol) of 2,2'-azobis(2,4-dimethylvaleronitrile) under nitrogen atmosphere to carry out polymerization reaction at 60 to 65° C. for 4 hours.

A reaction mixture obtained was dropwise added to methanol of about 20 mass per mass of the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 6.5 g of a polymer (f) comprising a repetitive unit shown below. The polymer (f) thus obtained had Mw of 12,800 and a dispersion degree of 1.82.

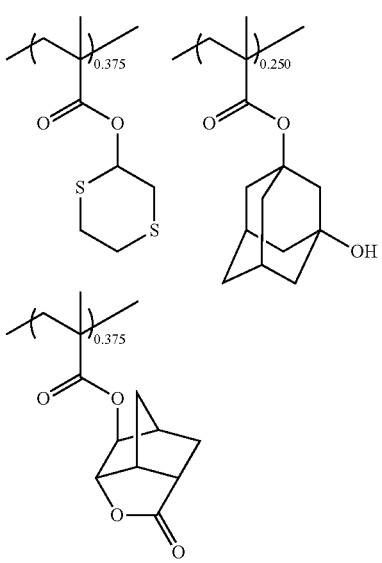

Synthetic Example 8

Synthesis of Polymer (g)

Polymerization reaction was carried out in the same charge amounts on the same conditions as in Synthetic Example 7, except that in Synthetic Example 7, 3.18 g (18.7 mmol) of α-methacryloyloxy-γ-butyrolactone was used in place of 4.16 g (18.7 mmol) of 5-methacryloyloxy-2,6-norbornanecarbolactone.

A reaction mixture obtained was dropwise added to methanol of about 20 mass per mass of the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 5.61 g of a polymer (g) comprising a repetitive unit shown below. The polymer (g) thus obtained had Mw of 11,900 and a dispersion degree of 1.65.

73

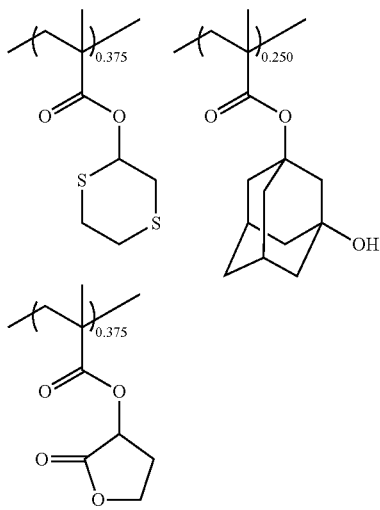

polymer (g)

Synthetic Example 9

Synthesis of Polymer (h)

A round-bottom flask having a content volume of 100 mL equipped with an electromagnetic stirring device, a reflux condenser and a thermometer was charged with 2.18 g (9.78 mmol) of 1,4-dithiepane-2-yl=methacrylate obtained in Example 5, 2.31 g (9.78 mmol) of 3-hydroxy-1-adamantyl=methacrylate, 42.0 g of 1,4-dioxane and 0.49 g (1.97 mmol) of 2,2'-azobis(2,4-dimethylvaleronitrile) under nitrogen atmosphere to carry out polymerization reaction at 60 to 65° C. for 4 hours.

A reaction mixture obtained was dropwise added to methanol of about 20 mass per mass of the reaction mixture at room temperature while stirring, and a precipitate produced was separated by filtering. The above precipitate was dissolved in 37.5 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.68 g of a polymer (h) comprising a repetitive unit shown below. The polymer (h) thus obtained had Mw of 14,400 and a dispersion degree of 1.59.

polymer (h)

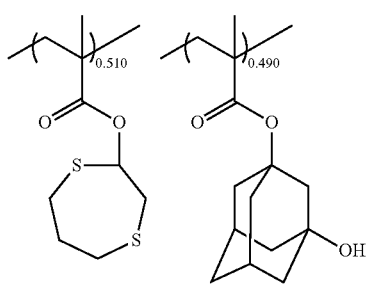

74

Synthetic Example 10

Synthesis of Polymer (i)

A round-bottom flask having a content volume of 100 mL equipped with an electromagnetic stirring device, a reflux condenser and a thermometer was charged with 2.09 g (9.35 mmol) of 1,4-dithiepane-2-yl=methacrylate obtained in Example 5, 1.48 g (6.25 mmol) of 3-hydroxy-1-adamantyl=methacrylate, 2.08 g (9.35 mmol) of 5-methacryloyloxy-2,6-norbornanecarbolactone, 50.0 g of 1,4-dioxane and 1.24 g (5.0 mmol) of 2,2'-azobis(2,4-dimethylvaleronitrile) under nitrogen atmosphere to carry out polymerization reaction at 60 to 65° C. for 4 hours.

A reaction mixture obtained was dropwise added to methanol of about 20 mass per mass of the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 3.09 g of a polymer (i) comprising a repetitive unit shown below. The polymer (i) thus obtained had Mw of 14,000 and a dispersion degree of 1.77.

polymer (i)

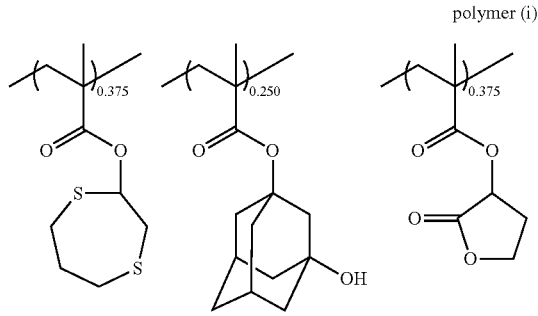

Synthetic Example 11

Synthesis of Polymer (j)

Polymerization reaction was carried out in the same charge amounts on the same conditions as in Synthetic Example 9, except that in Synthetic Example 9, 2.34 g (9.78 mmol) of 5,6-dimethyl-1,4-dithiane-2-yl=methacrylate obtained in Example 7 was used in place of 2.18 g (9.78 mmol) of 1,4-dithiepane-2-yl=methacrylate.

A reaction mixture obtained was dropwise added to methanol of about 20 mass per mass of the reaction mixture at room temperature while stirring, and a precipitate produced was separated by filtering. The above precipitate was dissolved in 37.5 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.76 g of a polymer (j) comprising a repetitive unit shown below. The polymer (j) thus obtained had Mw of 15,800 and a dispersion degree of 1.49.

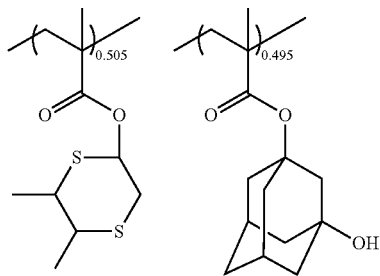

polymer (j)

Synthetic Example 12

Synthesis of Polymer (k)

Polymerization reaction was carried out in the same charge amounts on the same conditions as in Synthetic Example 10, except that in Synthetic Example 10, 2.23 g (9.35 mmol) of 5,6-dimethyl-1,4-dithiane-2-yl=methacrylate obtained in Example 7 was used in place of 2.09 g (9.35 mmol) of 1,4-dithiepane-2-yl=methacrylate.

A reaction mixture obtained was dropwise added to methanol of about 20 mass per mass of the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.69 g of a polymer (k) comprising a repetitive unit shown below. The polymer (k) thus obtained had Mw of 15,900 and a dispersion degree of 1.68.

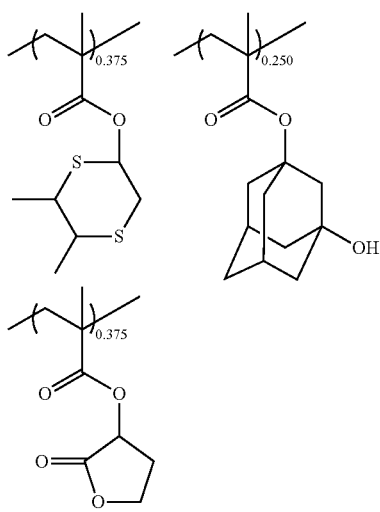

polymer (k)

Comparative Synthetic Example 1

Synthesis of Polymer (A)

A round-bottom flask having a content volume of 200 mL equipped with an electromagnetic stirring device, a reflux condenser and a thermometer was charged with 10.0 g (42.3 mmol) of 2-methyl-2-adamantyl=methacrylate, 10.0 g (42.7 mmol) of 3-hydroxy-1-adamantyl=methacrylate, 80.0 g of propylene glycol monomethyl ether and 1.40 g (8.53 mmol) of 2,2'-azobisisobutyronitrile under nitrogen atmosphere to carry out polymerization reaction at 81 to 87° C. for 2 hours.

A reaction mixture obtained was dropwise added to methanol of about 20 mass per mass of the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 13.2 g of a polymer (A) comprising a repetitive unit shown below. The polymer (A) thus obtained had Mw of 16,100 and a dispersion degree of 1.68.

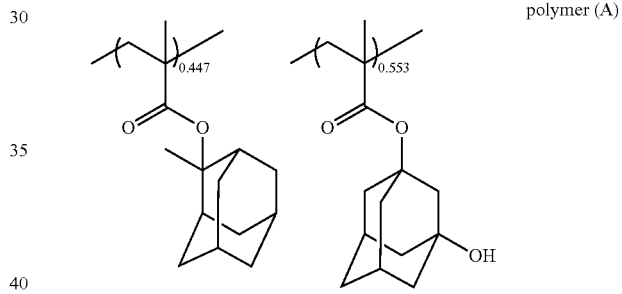

polymer (A)

Comparative Synthetic Example 2

Synthesis of Polymer (B)

Polymerization reaction was carried out in the same charge amounts on the same conditions as in Comparative Synthetic Example 1, except that in Comparative Synthetic Example 1, 7.39 g (42.7 mmol) of tetrahydropyran-2-yl=methacrylate was used in place of 10.0 g (42.3 mmol) of 2-methyl-2-adamantyl=methacrylate.

A reaction mixture obtained was dropwise added to methanol of about 20 mass per mass of the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 9.96 g of a polymer (B) comprising a repetitive unit shown below. The polymer (B) thus obtained had Mw of 13,200 and a dispersion degree of 1.71.

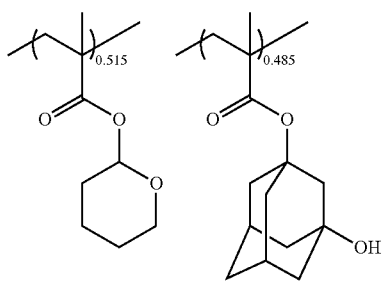

Comparative Synthetic Example 3

Synthesis of Polymer (C)

A round-bottom flask having a content volume of 200 mL equipped with an electromagnetic stirring device, a reflux condenser and a thermometer was charged with 9.14 g (50.2 mmol) of 1-methyl-1-cyclohexyl=methacrylate, 11.82 g (50.0 mmol) of 3-hydroxy-1-adamantyl=methacrylate, 101.4 g of 1,4-dioxane and 1.24 g (7.55 mmol) of 2,2'-azobisisobutyronitrile under nitrogen atmosphere to carry out polymerization reaction at 80 to 82° C. for 5 hours.

A reaction mixture obtained was dropwise added to a water-methanol mixed solution (mass ratio water:methanol=1:3) of about 20 mass per mass of the reaction mixture at room temperature while stirring, and a precipitate produced was separated by filtering. The above precipitate was dissolved in 140.0 g of THF, and the solution prepared was dropwise added to the water-methanol mixed solution (mass ratio water:methanol=1:3) of the same mass as described above while stirring. A precipitate produced was separated by filtering and then washed with the water-methanol mixed solution (mass ratio water:methanol=1:3) of the same mass as described above, whereby a white precipitate was obtained. The above precipitate was dried at 50° C. for 10 hours under reduced pressure (26.7 Pa) to obtain 11.8 g of a polymer (C) comprising a repetitive unit shown below. The polymer (C) thus obtained had Mw of 12,600 and a dispersion degree of 1.83.

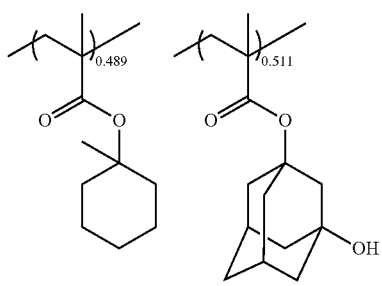

Comparative Synthetic Example 4

Synthesis of Polymer (D)

A round-bottom flask having a content volume of 100 mL equipped with an electromagnetic stirring device, a reflux condenser and a thermometer was charged with 4.39 g (18.7 mmol) of 2-methacryloyloxy-2-methyladamantane, 2.95 g (12.5 mmol) of 3-hydroxy-1-adamantyl-methacrylate, 3.18 g (18.7 mmol) of α-methacryloyloxy-γ-butyrolactone, 35.4 g of methyl ethyl ketone and 0.66 g (4.0 mmol) of 2,2'-azobisisobutyronitrile under nitrogen atmosphere to carry out polymerization reaction at 80° C. for 4 hours.

A reaction mixture obtained was dropwise added to methanol of about 20 mass per mass of the reaction mixture at room temperature while stirring, whereby a white precipitate was obtained. The above precipitate was separated by filtering and dried at 50° C. for 10 hours under reduced pressure (26.7 Pa) to obtain 6.06 g of a polymer (D) comprising a repetitive unit shown below. The polymer (D) thus obtained had Mw of 10,000 and a dispersion degree of 1.50.

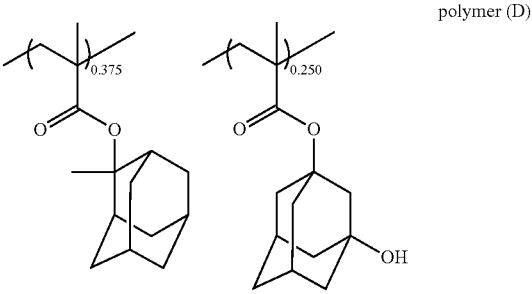

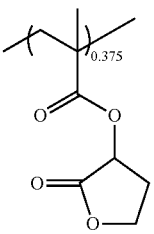

Comparative Synthetic Example 5

Synthesis of Polymer (E)

Polymerization reaction was carried out in the same charge amounts on the same conditions as in Comparative Synthetic Example 4, except that in Comparative Synthetic Example 4, 3.18 g (18.7 mmol) of tetrahydropyran-2-yl=methacrylate was used in place of 4.39 g (18.7 mmol) of 2-methacryloyloxy-2-methyladamantane.

A reaction mixture obtained was dropwise added to methanol of about 20 mass per mass of the reaction mixture at room temperature while stirring, whereby a white precipitate was obtained. The above precipitate was separated by filtering and dried at 50° C. for 10 hours under reduced pressure (26.7 Pa) to obtain 5.82 g of a polymer (E) comprising a repetitive unit shown below. The polymer (E) thus obtained had Mw of 6,500 and a dispersion degree of 1.60.

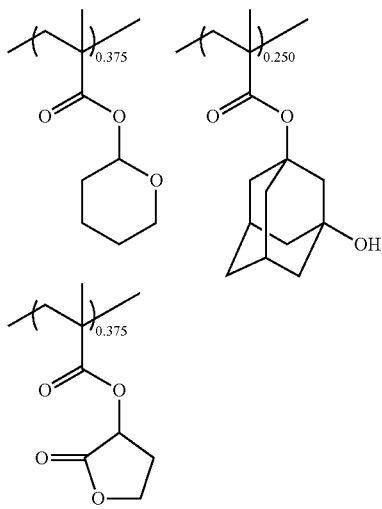

polymer (E)

Comparative Synthetic Example 6

Synthesis of Polymer (F)

Polymerization reaction was carried out in the same charge amounts on the same conditions as in Comparative Synthetic Example 4, except that in Comparative Synthetic Example 4, 3.41 g (18.7 mmol) of 1-methyl-1-cyclohexyl=methacrylate was used in place of 4.39 g (18.7 mmol) of 2-methacryloyloxy-2-methyladamantane.

A reaction mixture obtained was dropwise added to methanol of about 20 mass per mass of the reaction mixture at room temperature while stirring, whereby a white precipitate was obtained. The above precipitate was separated by filtering and dried at 50° C. for 10 hours under reduced pressure (26.7 Pa) to obtain 5.69 g of a polymer (F) comprising a repetitive unit shown below. The polymer (F) thus obtained had Mw of 6,900 and a dispersion degree of 1.58.

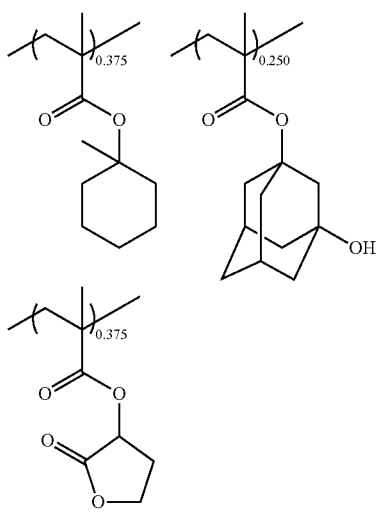

polymer (F)

Comparative Synthetic Example 7

Synthesis of Polymer (G)

Polymerization reaction was carried out in the same charge amounts on the same conditions as in Comparative Synthetic Example 1, except that in Comparative Synthetic Example 1, 8.98 g (42.7 mmol) of 1,3-dithiane-5-yl=methacrylate was used in place of 10.0 g (42.3 mmol) of 2-methyl-2-adamantyl=methacrylate.

A reaction mixture obtained was dropwise added to methanol of about 20 mass per mass of the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 10.22 g of a polymer (G) comprising a repetitive unit shown below. The polymer (G) thus obtained had Mw of 15,200 and a dispersion degree of 1.69.

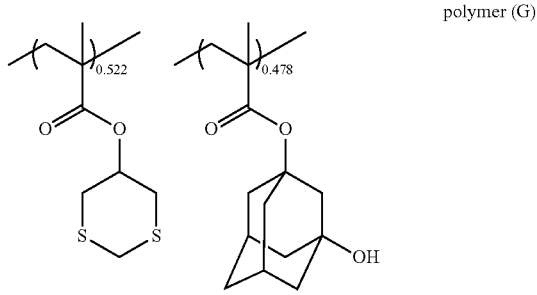

polymer (G)

Comparative Synthetic Example 8

Synthesis of Polymer (H)

Polymerization reaction was carried out in the same charge amounts on the same conditions as in Comparative Synthetic Example 4, except that in Comparative Synthetic Example 4, 3.93 g (18.7 mmol) of 1,3-dithiane-5-yl=methacrylate was used in place of 4.39 g (18.7 mmol) of 2-methacryloyloxy-2-methyladamantane.

A reaction mixture obtained was dropwise added to methanol of about 20 mass per mass of the reaction mixture at room temperature while stirring, whereby a white precipitate was obtained. The above precipitate was separated by filtering and dried at 50° C. for 10 hours under reduced pressure (26.7 Pa) to obtain 5.99 g of a polymer (H) comprising a repetitive unit shown below. The polymer (H) thus obtained had Mw of 12,800 and a dispersion degree of 1.65.

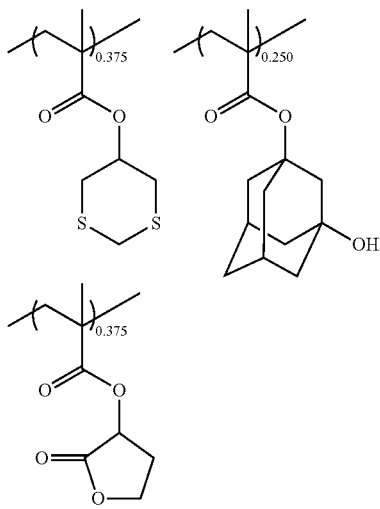

polymer (H)

Examples 14 to 23 and Comparative Examples 1 to 8

Evaluation of Dissolution Characteristics in Developer by QCM Method

Used were 100 parts by mass of the polymer obtained in Synthetic Examples 3 to 12 or Comparative Synthetic Examples 1 to 8, 3 parts by mass of TPS-109 (trade name, component: triphenylsulfonium nonafluoro-n-butane-sulfonate, manufactured by Midori Kagaku Co., Ltd.) as a photoacid generator and as solvents, ethyl lactate when the polymer (b), (c), (d), (e), (h), (j), (A), (B), (C) and (G) were used and a mixed solvent of propylene glycol monomethyl ether acetate/ethyl lactate=1/1 (volume ratio) when the polymer other than above ones were used, and the respective components were mixed to prepare photoresist compositions in which a concentration of the polymer was 12% by mass.

The respective photoresist compositions thus obtained were filtrated through a filter (made of a tetrafluoroethylene resin (PTFE), pore diameter: 0.2 μm), and then they were coated respectively by a spin coating method on a quartz substrate of a 1 inch size in which a gold electrode was vacuum-deposited on a surface to form a photosensitive layer having a thickness of 300 nm. The quartz substrate having a photosensitive layer formed thereon was pre-baked at 110° C. for 90 seconds on a hot plate and then exposed at an exposure dose of 100 mJ/cm² with an ArF excimer laser (wavelength: 193 nm), and subsequently it was subjected to post-exposure baking at 110° C. for 90 seconds.

The quartz substrate described above was set in a quartz oscillator microbalance equipment "RQCM" (trade name; manufactured by Maxtek Corp.) and subjected to developing treatment by a tetramethylammonium hydroxide aqueous solution of 2.38% by mass for 120 seconds. A change in an oscillation frequency of the quartz substrate during the developing treatment was monitored with the passage of time, and then a change in the oscillation frequency was reduced to a change in the film thickness to calculate the maximum swelling amount from a change in an increase of the film thickness and calculate the dissolution rate from a change in a decrease of the film thickness. The results thereof are shown in Table 5.

TABLE 5 evaluation of dissolution characteristics in developer by QCM method

| Polymer in photoresist composition | | Dissolution rate in developing (nm/second) | Maximum swelling amount (nm) |
|---|---|---|---|
| Example 14 | (b) | 1200 | 10 |
| Example 15 | (c) | 1240 | 10 |
| Example 16 | (d) | 1240 | 8 |
| Example 17 | (e) | 1300 | 8 |
| Example 18 | (f) | 1100 | 11 |
| Example 19 | (g) | 1220 | 9 |
| Example 20 | (h) | 1190 | 11 |
| Example 21 | (i) | 1290 | 9 |
| Example 22 | (j) | 1240 | 11 |
| Example 23 | (k) | 1340 | 9 |
| Comparative Example 1 | (A) | 950 | 100 |
| Comparative Example 2 | (B) | 1200 | 10 |
| Comparative Example 3 | (C) | 500 | 20 |
| Comparative Example 4 | (D) | 600 | 40 |
| Comparative Example 5 | (E) | 1100 | 10 |
| Comparative Example 6 | (F) | 530 | 10 |
| Comparative Example 7 | (G) | Not dissolved | — |
| Comparative Example 8 | (H) | Not dissolved | — |

Examples 24 to 33 and Comparative Examples 9 to 16

Evaluation of Exposure by Two-Beam Interference Method

Used were 100 parts by mass of the polymer obtained in Synthetic Examples 3 to 12 or Comparative Synthetic Examples 1 to 8, 3 parts by mass of TPS-109 (trade name, component: triphenylsulfonium nonafluoro-n-butane-sulfonate, manufactured by Midori Kagaku Co., Ltd.) as a photoacid generator and as solvents, ethyl lactate when the polymer (b), (c), (d), (e), (h), (j), (A), (B), (C) and (G) were used and a mixed solvent of propylene glycol monomethyl ether acetate/ethyl lactate 1/1 (volume ratio) when the polymer other than above ones were used, and the respective components were mixed to prepare photoresist compositions in which a concentration of the polymer was 12% by mass.

The respective photoresist compositions thus obtained were filtrated through a filter (made of a tetrafluoroethylene resin (PTFE), pore diameter: 0.2 μm). A propylene glycol monomethyl ether acetate solution of a cresol novolac resin (PS-6937, manufactured by Gunei Chemical Industry Co., Ltd.) having a concentration of 6% by mass was coated on a silicon wafer having a diameter of 10 cm by a spin coating method and baked at 200° C. for 90 seconds on a hot plate to thereby form a anti-reflective coat (undercoat film), and the above filtrates were coated respectively on the above silicon wafer by a spin coating method and pre-baked at 130° C. for 90 seconds on a hot plate to thereby form a resist film having a film thickness of about 300 nm.

The above resist film was exposed with an ArF excimer laser having a wavelength of 193 nm by a two-beam interference method. Subsequently, it was subjected to post-exposure baking at 130° C. for 90 seconds and then to developing treatment for 60 seconds by a 2.38 mass % tetramethylammonium hydroxide aqueous solution to thereby form a line and space pattern of 1:1. A piece obtained by cutting the wafer subjected to the development was observed under a scanning electron microscope (SEM) to observe a form of the pattern in an exposure dose in which the line and space having a line width of 100 nm was subjected to resolution by 1:1 and measure a change in the line width (hereinafter referred to as LWR). The line width was detected in plural positions in a measuring monitor, and dispersion (3σ) in variation of the detected positions was set to an index for LWR. The results thereof are shown in Table 6.

TABLE 6 evaluation of exposure by two-beam interference method

| | Polymer in photoresist composition | LWR (nm) | Pattern form |
|---|---|---|---|
| Example 24 | (b) | 8.0 | Good |
| Example 25 | (c) | 7.8 | Good |
| Example 26 | (d) | 7.2 | Good |
| Example 27 | (e) | 7.1 | Good |
| Example 28 | (f) | 7.5 | Good |
| Example 29 | (g) | 7.3 | Good |
| Example 30 | (h) | 7.9 | Good |
| Example 31 | (i) | 7.5 | Good |
| Example 32 | (j) | 8.0 | Good |
| Example 33 | (k) | 7.4 | Good |
| Comparative Example 9 | (A) | 13.4 | Good |
| Comparative Example 10 | (B) | 8.1 | Good |
| Comparative Example 11 | (C) | 10.1 | Good |
| Comparative Example 12 | (D) | 12.3 | Good |
| Comparative Example 13 | (E) | 8.5 | Good |
| Comparative Example 14 | (F) | 9.3 | Good |
| Comparative Example 15 | (G) | Unable to form pattern | — |
| Comparative Example 16 | (H) | Unable to form pattern | — |

Examples 34 to 41 and Comparative Examples 17 to 21

Evaluation of Heat Stability

The heat stabilities of the respective polymer obtained in Synthetic Examples 3 to 6 and 9 to 12 or Comparative Synthetic Examples 1 to 3, 7 and 8 were confirmed by means of a micro heat weight measuring equipment "TGA-50" (trade name; manufactured by Shimadzu Corporation).

A sample amount of the polymer was set to about 5.0 mg, and the heat stability was measured at a nitrogen gas flow rate of 50 mL/minute and a heating rate of 10° C./minute in a range of 20 to 600° C. The temperature at which a reduction in the weight was initiated and the temperature at which the weight was reduced by 5% based on the original weight were read from a graph obtained. A reduction in the weight shows that the polymer is decomposed by heat, and it can usually be understood that the higher the temperature at which a reduction in the weight is shown is, the more stable the polymer is to heat. The results thereof are shown in Table 7.

TABLE 7 evaluation of heat stability

| | Polymer in photoresist composition | Decomposition initiating temperature (° C.) | Temperature in 5% weight reduction (° C.) |
|---|---|---|---|
| Example 34 | (b) | 170 | 203 |
| Example 35 | (c) | 160 | 197 |
| Example 36 | (d) | 140 | 201 |
| Example 37 | (e) | 170 | 200 |
| Example 38 | (h) | 170 | 208 |
| Example 39 | (i) | 170 | 213 |
| Example 40 | (j) | 160 | 200 |
| Example 41 | (k) | 160 | 208 |
| Comparative Example 17 | (A) | 190 | 227 |
| Comparative Example 18 | (B) | 120 | 162 |
| Comparative Example 19 | (C) | 180 | 209 |
| Comparative Example 20 | (G) | 170 | 192 |
| Comparative Example 21 | (H) | 170 | 195 |

It can be found from the results shown in Table 5 to Table 7 that in the case of the polymer containing the acrylic ester derivative (1) of the present invention in a constitutional unit, a dissolution rate in an alkali developer used in a developing step when a pattern is formed on the photoresist is very high as compared with the case of the polymer containing no acrylic ester derivative (1) of the present invention in a constitutional unit and that they have a very small maximum swelling amount in developing (refer to Examples 14 to 23 and Comparative Examples 1 to 8) and are improved in LWR (refer to Examples 24 to 33 and Comparative Examples 9 to 16). Further, they are excellent as well in a heat stability (refer to Examples 34 to 41 and Comparative Examples 17 to 21), and therefore it can be found that they are useful as a chemically amplified resist for producing semiconductor devices.

Reference Example 2

Preparation of Photoresist Composition b

The polymer (b) 100 parts by mass obtained in Synthetic Example 3, triphenylsulfonium nonafluoro-n-butanesulfonate 3.0 parts by mass as a photoacid generator, N-(tert-butoxycarbonyl)pyrrolidine 0.27 part by mass as a basic compound and cyclohexanone 1962 parts by mass as a solvent were mixed to obtain a solution in which the respective components were homogeneously mixed. Then, the solution obtained above was filtrated through a membrane filter having a pore diameter of 0.2 μm to prepare a photoresist composition (b) (whole solid matter concentration: about 5% by mass).

Measurement of Refractive Index:

The photoresist composition (b) prepared above was spin-coated on a silicon wafer by means of "CLEAN TRACK ACTS" manufactured by Tokyo Electron Limited and pre-baked at 100° C. for 60 seconds to form a resist film having a film thickness of 120 nm.

A refractive index of the above resist film in a wavelength of 193 nm was measured by means of a spectroscopic ellipsometer ("VUV-VASE", manufactured by J. A. Woollam Co., Inc.). The results thereof are shown in Table 8.

Reference Examples 3 to 9

Preparation of Photoresist Compositions (d) and (f) to (k)

The experiment was carried out in the same manner as in Reference Example 2 to prepare respectively photoresist compositions (d) and (f) to (k) (whole solid matter concentration: about 5% by mass) and measure refractive indices thereof in a wavelength of 193 nm, except that in Reference Example 2, the polymer (d) and (f) to (k) obtained in Synthetic Examples 5 and 7 to 12 were used in place of the polymer (b). The results thereof are shown in Table 8.

Reference Examples 10 to 17

Preparation of Photoresist Compositions (A) to (H)

The experiment was carried out in the same manner as in Reference Example 2 to prepare respectively photoresist compositions (A) to (H) (whole solid matter concentration: about 5% by mass) and measure refractive indices thereof in a wavelength of 193 nm, except that in Reference Example 2, the polymer (A) to (H) obtained in Comparative Synthetic Examples 1 to 8 were used in place of the polymer (b). The results thereof are shown in Table 8.

TABLE 8 measurement of refractive index

| | Photoresist composition | Refractive index |
|---|---|---|
| Reference Example 2 | (b) | 1.77 |
| Reference Example 3 | (d) | 1.77 |
| Reference Example 4 | (f) | 1.75 |
| Reference Example 5 | (g) | 1.75 |
| Reference Example 6 | (h) | 1.75 |
| Reference Example 7 | (i) | 1.75 |
| Reference Example 8 | (j) | 1.74 |
| Reference Example 9 | (k) | 1.74 |
| Reference Example 10 | (A) | 1.70 |
| Reference Example 11 | (B) | 1.70 |
| Reference Example 12 | (C) | 1.70 |
| Reference Example 13 | (D) | 1.71 |
| Reference Example 14 | (E) | 1.71 |
| Reference Example 15 | (F) | 1.71 |
| Reference Example 16 | (G) | 1.75 |
| Reference Example 17 | (H) | 1.75 |

Resist films generally used at present have a refractive index of 1.69 to 1.71 in many cases, and such resist films do not involve the problem that exposure light is less liable to be incident into a photoresist film when water (a refractive index: 1.44 in a wavelength of 193 nm) is used as an immersion liquid. However, when an immersion liquid of a next generation (an immersion liquid having a refractive index of 1.71 or more) having a larger refractive index than that of water is used in the future, exposure light is less liable to be sufficiently incident into a photoresist film in the case of the above resist films generally used, and desired resist patterns are not obtained. However, according to the photoresist composition (9) containing the polymer (8) containing the acrylic ester derivative (1) of the present invention in a structural unit, exposure light is not reflected in an interface between the immersion liquid and the photoresist film as well in a liquid immersion lithographic step in which the above immersion liquid of a next generation is used in place of water, and it can sufficiently be incident into the photoresist film.

Reference Example 18

Characteristic Curve Measurement

A layer of anti-reflective coat ("ARC29A", manufactured by Bulwer Science Inc.) having a film thickness of 77 nm was formed on an 8 inch silicon wafer used by means of "CLEAN TRACK ACT8" manufactured by Tokyo Electron Limited. The photoresist composition (b) obtained in Reference Example 2 was spin-coated on the layer of anti-reflective coat formed above by means of "CLEAN TRACK ACT8" (manufactured by Tokyo Electron Limited.) and pre-baked at 100° C. for 60 seconds to form a resist film having a film thickness of 120 nm.

The above resist film was exposed by means of an ArF excimer laser exposing equipment ("NSR S306C", manufactured by Nikon Corporation, illumination condition: NA 0.78 sigma 0.90/0.52). This exposure was carried out through quartz provided with no patterns.

Thereafter, the resist film was subjected to post-exposure baking at 130° C. for 60 seconds and then developed by a tetramethylammonium hydroxide aqueous solution of 2.38% by mass at 23° C. for 60 seconds. After developing, the film was washed with water and dried to obtain a wafer for measuring a characteristic curve.

Then, the film thicknesses of the resist films obtained at the respective exposure doses were measured by means of an automatic film thickness measuring equipment ("VM-2010", manufactured by Dainippon Screen Mfg. Co., Ltd.) to confirm correlation between the exposure dose (mJ/cm$^2$) and the film thickness (angstrom (Å)). The results thereof are shown in FIG. 1.

Reference Example 19

Characteristic Curve Measurement

The measurement was carried out in the same manner, except that in Reference Example 18, the photoresist composition (d) obtained in Reference Example 3 was used in place of the photoresist composition (b). The results thereof are shown in FIG. 1.

It can be confirmed from FIG. 1 that a photoresist film formed by the photoresist composition (9) containing the polymer (8) containing the acrylic ester derivative (1) in a structural unit is decreased in a residual film thickness by increasing an exposure dose to make the whole photoresist film soluble in a developer at a prescribed exposure dose, and it has been found that the exposure latitude (variation in a line width versus a change in an exposure dose) is good (refer to Reference Examples 18 and 19). Accordingly, a coating film formed by the photoresist composition (9) containing the polymer (8) containing the acrylic ester derivative (1) in a structural unit can sufficiently be subjected to patterning for a photoresist film, and the contrast is expected to be sufficiently obtained.

As shown above, the photoresist composition (9) containing the polymer (8) containing the acrylic ester derivative (1) of the present invention in a structural unit makes it possible to form a photoresist film having a high sensitivity, and the polymer (8) obtained by using the acrylic ester derivative (1) of the present invention is useful as a chemically amplified resist for producing semiconductor devices.

INDUSTRIAL APPLICABILITY

The acrylic ester derivative (1) obtained in the present invention is useful as a raw material for the polymer (8) added to the photoresist composition (9). Further, the alcohol (5) and the ester (6) each obtained in the present invention are useful as a raw material for the above acrylic ester derivative (1).

The invention claimed is:

1. A process for producing an acrylic ester derivative, the process comprising, in the following order:

(I) reacting a dithiol of formula (2) with a base:

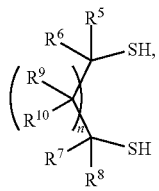

(2)

wherein in n, $R^5$, $R^6$, $R^7$, $R^8$, $R^9$, and $R^{10}$:
1) when n is 0, $R^5$ and $R^8$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms; $R^6$ and $R^7$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms or $R^6$ and $R^7$ together form an alkylene group comprising 3 to 6 carbon atoms; or
2) when n is 1 or 2, $R^5$, $R^6$, $R^7$, $R^8$, $R^9$, and $R^{10}$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms, to obtain a reaction product;

(II) reacting the reaction product with halide of formula (4):

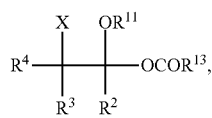

(4)

wherein:
$R^2$, $R^3$, and $R^4$ together satisfy any of:
1) $R^2$, $R^3$ and $R^4$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms;
2) $R^2$ and $R^3$ together form an alkylene group comprising 3 to 6 carbon atoms, and $R^4$ is a hydrogen atom, a linear alkyl group comprising 1 to 6 carbon atoms, a branched alkyl group comprising 3 to 6 carbon atoms, or a cyclic alkyl group comprising 3 to 6 carbon atoms; or
3) $R^2$ is a hydrogen atom, a linear alkyl group comprising 1 to 6 carbon atoms, a branched alkyl group comprising 3 to 6 carbon atoms, or a cyclic alkyl group comprising 3 to 6 carbon atoms, and $R^3$ and $R^4$ together form an alkylene group comprising 3 to 6 carbon atoms;

$R^{11}$ is a linear alkyl group comprising 1 to 3 carbon atoms or a branched alkyl group comprising 3 to 6 carbon atoms;
X is a chlorine atom, a bromine atom, or an iodine atom; and
$R^{13}$ is a linear alkyl group comprising 1 to 6 carbon atoms, a branched alkyl group comprising 3 to 6 carbon atoms, or a cyclic alkyl group comprising 3 to 6 carbon atoms, to obtain an ester of formula (6):

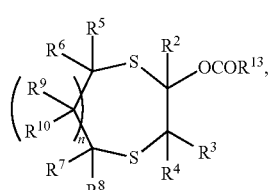

(6)

wherein n, $R^1$, $R^2$, $R^3$, $R^4$, $R^5$, $R^6$, $R^7$, $R^8$, $R^9$, $R^{10}$, and $R^{13}$ are the same as above;

(III) hydrolyzing the ester of formula (6), to obtain an alcohol of formula (5):

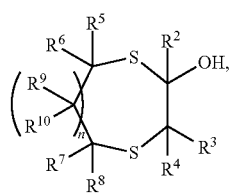

(5)

wherein n, $R^2$, $R^3$, $R^4$, $R^5$, $R^6$, $R^7$, $R^8$, $R^9$, and $R^{10}$ are the same as above; and (IV) reacting the alcohol of formula (5), in the presence of a basic substance, with a polymerizable group-introducing agent having a formula selected from the group consisting of:

$CH_2=CR^1COX^1$;

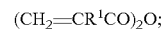

$(CH_2=CR^1CO)_2O$;

$CH_2=CR^1COOC(=O)R^{14}$; and

$CH_2=CR^1COOSO_2R^{15}$;

wherein:
$R^1$ is a hydrogen atom, methyl, or trifluoromethyl;
$X^1$ is a chlorine atom, a bromine atom, or an iodine atom;
$R^{14}$ is t-butyl or 2,4,6-trichlorophenyl; and
$R^{15}$ is methyl or p-tolyl, thereby obtaining an acrylic ester derivative of formula (1):

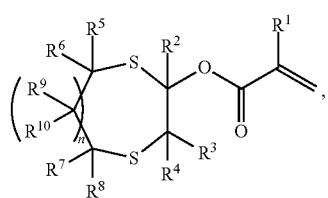

(1)

wherein n, $R^1$, $R^2$, $R^3$, $R^4$, $R^5$, $R^6$, $R^7$, $R^8$, $R^9$, and $R^{10}$ are the same as above.

2. The process of claim 1, wherein the base reacted with the dithiol is sodium hydride.

3. A process for producing an acrylic ester derivative, the process comprising, in the following order:

(I) reacting a base with dithiol of formula (2):

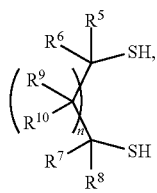 (2)

wherein in n, $R^5$, $R^6$, $R^7$, $R^8$, $R^9$, and $R_{10}$:
1) when n is 0, $R^5$ and $R^8$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms; $R^6$ and $R^7$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms or $R^6$ and $R^7$ together form an alkylene group comprising 3 to 6 carbon atoms; or
2) when n is 1 or 2, $R^5$, $R^6$, $R^7$, $R^8$, $R^9$, and $R^{10}$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms, to obtain a reaction product;

(II) reacting the reaction product with a halide of formula (4):

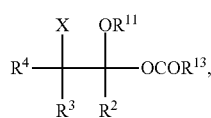 (4)

wherein:
$R^2$, $R^3$, and $R^4$ together satisfy any of:
1) $R^2$, $R^3$ and $R^4$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms;
2) $R^2$ and $R^3$ together form an alkylene group comprising 3 to 6 carbon atoms, and $R^4$ is a hydrogen atom, a linear alkyl group comprising 1 to 6 carbon atoms, a branched alkyl group comprising 3 to 6 carbon atoms, or a cyclic alkyl group comprising 3 to 6 carbon atoms; or
3) $R^2$ is a hydrogen atom, a linear alkyl group comprising 1 to 6 carbon atoms, a branched alkyl group comprising 3 to 6 carbon atoms, or a cyclic alkyl group comprising 3 to 6 carbon atoms, and $R^3$ and $R^4$ together form an alkylene group comprising 3 to 6 carbon atoms; and $R^{11}$ is a linear alkyl group comprising 1 to 3 carbon atoms or a branched alkyl group comprising 3 to 6 carbon atoms;

X is a chlorine atom, a bromine atom, or an iodine atom; and $R^{13}$ is a linear alkyl group comprising 1 to 6 carbon atoms, a branched alkyl group comprising 3 to 6 carbon atoms, or a cyclic alkyl group comprising 3 to 6 carbon atoms, to obtain alcohol of formula (5):

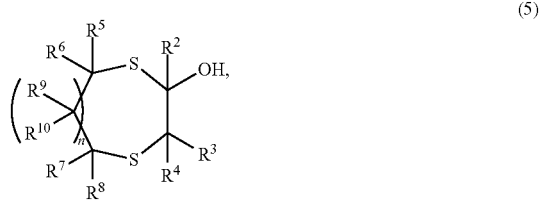 (5)

wherein n, $R^2$, $R^3$, $R^4$, $R^5$, $R^6$, $R^7$, $R^8$, $R^9$, and $R^{10}$ are the same as above; and (III) reacting alcohol of formula (5), in the presence of a basic substance, with a polymerizable group-introducing agent having a formula selected from the group consisting of:

wherein:
$R^1$ is a hydrogen atom, methyl, or trifluoromethyl;
$X^1$ is a chlorine atom, a bromine atom, or an iodine atom;
$R^{14}$ is t-butyl or 2,4,6-trichlorophenyl; and
$R^{15}$ is methyl or p-tolyl,
thereby obtaining an acrylic ester derivative of formula (1):

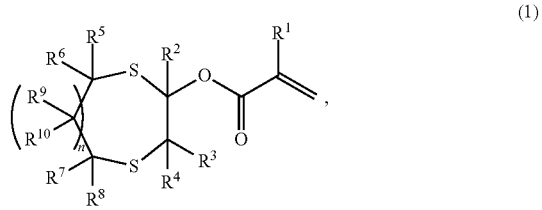 (1)

wherein n, $R^1$, $R^2$, $R^3$, $R^4$, $R^5$, $R^6$, $R^7$, $R^8$, $R^9$, and $R^{10}$ are the same as above.

4. The process of claim 3, wherein the base reacted with the dithiol is sodium hydride.

* * * * *